US008217157B2

(12) United States Patent
Chaudhry et al.

(10) Patent No.: US 8,217,157 B2
(45) Date of Patent: Jul. 10, 2012

(54) COMPOSITIONS AND METHODS FOR TREATING AND PREVENTING HEART TISSUE DEGENERATION, AND USES THEREOF

(75) Inventors: Hina W. Chaudhry, New York, NY (US); Debra J. Wolgemuth, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 565 days.

(21) Appl. No.: 10/557,873

(22) PCT Filed: May 18, 2004

(86) PCT No.: PCT/US2004/015691
§ 371 (c)(1),
(2), (4) Date: Aug. 29, 2006

(87) PCT Pub. No.: WO2005/000403
PCT Pub. Date: Jan. 6, 2005

(65) Prior Publication Data
US 2007/0014766 A1    Jan. 18, 2007

Related U.S. Application Data

(60) Provisional application No. 60/471,952, filed on May 19, 2003.

(51) Int. Cl.
C07H 21/02 (2006.01)
C07H 21/04 (2006.01)
A61K 48/00 (2006.01)
(52) U.S. Cl. .......................................... 536/23.1; 514/44
(58) Field of Classification Search .................. None
See application file for complete search history.

(56) References Cited

U.S. PATENT DOCUMENTS

| | | | |
|---|---|---|---|
| 5,973,119 A * | 10/1999 | Coats et al. ................... 530/350 |
| 6,150,584 A | 11/2000 | Kucherlapati et al. |
| 6,162,963 A | 12/2000 | Kucherlapati et al. |
| 6,278,039 B1 | 8/2001 | Johnson et al. |
| 6,448,080 B1 | 9/2002 | Ward et al. |
| 6,491,905 B1 | 12/2002 | Sorscher et al. |
| 6,534,052 B1 | 3/2003 | Xiao et al. |
| 2002/0006664 A1 | 1/2002 | Sabatini et al. |
| 2002/0166134 A1 | 11/2002 | Field et al. |
| 2002/0197240 A1 | 12/2002 | Chiu |
| 2003/0017549 A1 | 1/2003 | Owens |
| 2003/0018993 A1 | 1/2003 | Gutterson et al. |
| 2003/0022367 A1 | 1/2003 | Xu et al. |
| 2003/0054973 A1 | 3/2003 | Anversa |

FOREIGN PATENT DOCUMENTS

| | | |
|---|---|---|
| WO | WO 99/32619 | 7/1999 |
| WO | WO 00/78119 | * 12/2000 |
| WO | WO 01/29058 | 4/2001 |
| WO | WO 01/68836 | 9/2001 |
| WO | WO 01/96584 | 12/2001 |

OTHER PUBLICATIONS

Wilson et al. Adv. Drug Deliv. Rev. 46:205-209; 2001.*
Thomas et al. Nature Rev./Genet. 4: 346-358; 2003.*
Brockstedt et al. Clinical Immunol. 92:67-75; 1999.*
Niidome et al. Gene Therapy 9:1647-1652; 2002.*
Murphy et al. Nature Genetics 15:83-86; 1997.*
Haddad et al. BBRC 274:188-196; 2000.*
Wang et al., 1990, Nature 343: 555-557.*
Kang and Koh, Differential and dramatic changes of cyclin-dependent kinase activities in cardiomyocytes during the neonatal period, J Mol Cell Cardiol, 1997, 29(7):1767-1777.
Li et al, Rapid transition of cardiac myocytes from hyperplasia to hypertrophy during postnatal development, J Mol Cell Cardiol, 1996, 28:1737-1746.
Mendez and Keys, Density and composition of mammalian muscle, Metabolism, 1960, 9:184-188.
Parker and Schneider, Growth factors, proto-oncogenes, and plasticity of the cardiac phenotype, Annu Rev Physiol, 1991, 53:179-200.
Poolman and Brooks. CIP/KIP cyclin-dependent kinase inhibitor (CDKI) expression during cardiac myocyte development (Abstract), Mol Cell Cardiol, 1997, 29:A19.
Poolman et al, Altered expression of cell cycle proteins and prolonged duration of cardiac myocyte hyperplasia in p27 knockout mice, Circ Res, 1999, 85:117-127.
Poss et al, Heart regeneration in zebrafish, Science, 2002, 298:2188-2190.
Sherr and Roberts, Inhibitors of mammalian G1 cyclin-dependent kinases, Genes Dev, 1995, 9:1149-1163. Simpson, Proto-oncogenes and cardiac hypertrophy. Annu Rev Physiol, 1989, 51:189-202.
Slawson et al, Cardiac MRI of the normal and hypertrophied mouse heart, Magn. Reson Med, 1998, 39:980-987.
Subramaniam et al, Tissue specific regulation of the alpha-myosin heavy chain gene promoter in transgenic mice, J Biol Chem, 1991, 266:24613-24620.
Supplementary European Search Report issued Jun. 19, 2009, in the related application EP 04752668.
Engel et al, p21CIP1 controls proliferating cell nuclear antigen level in adult cardiomyocytes, Molecular and Cellular Biology, 2003, 23:555-565.
Agah et al., J Clin. Invest., 100:2722-28, 1997.

(Continued)

*Primary Examiner* — Joanne Hama
(74) *Attorney, Agent, or Firm* — SNR Denton US LLP

(57) ABSTRACT

The present invention provides methods for promoting generation of heart tissue, and for treating and preventing heart tissue degeneration. Additionally, the present invention provides a therapeutic composition comprising a cyclin-associated agent, and a kit comprising the composition. The present invention further provides a heart tissue cell, a sidepopulation progenitor cell, and a stem cell in which cyclin is augmented. Also provided are cell lines comprising these cells, screening methods using the cell lines, and drugs identified by these methods. The present invention further provides in vitro systems for use in screening candidate drugs for at least one cardiotoxic effect and/or for synergy with cyclin in the treatment and prevention of heart tissue degeneration. Finally, the present invention provides use of a cyclin-associated agent in the generation of heart tissue, and use of a cyclin associated agent in the treatment or prevention of heart tissue degeneration.

22 Claims, 15 Drawing Sheets

OTHER PUBLICATIONS

Ashrafi et al., Genome wide RNAi analysis of Caenorhabditis elegans fat regulatory genes. Nature, 421:268-72, 2003; (Abstract Only).

Behringer et al., Sequences 5' of the homeobox of the Hox-1.4 gene direct tissue-specific expression of lacZ during mouse development Development, 117:823-33, 1993.

Beinlich and Morgan, Control of growth in neonatal pig hearts Mol. Cell. Biochem., 119:3-9, 1993 (Abstract Only).

Beltrami et al., Evidence that human cardiac myocytes divide after myocardial infarction N. Engl. J. Med., 344(23):1750-57, 2001 (Abstract Only).

Bianchi et al., Biochemical and structural evidence for pig myocardium adherens junction disruption by cardiopulmonary bypass Circulation, 104(12 Suppl. 1):I319-24,2001.

Billy et al., Specific interference with gene expression induced by long, double-stranded RNA in mouse embryonal teratocarcinoma cell lines. Proc. Nat. Acad. Sci. USA, 98:14428-33, 2001.

Brooks et al. Expression and Activities of Cyclins and Cyclin-dependent Kinases in Developing Rat Ventricular Myocytes. J.Mol. Cell. Cardiol. 1997.

Brooks et al, Arresting developments in the cardiac myocyte cell cycle: role of cyclin-dependent kinase inhibitors Cardiovasc. Res., 39:301-11, 1998 (Abstract Only).

Casscells et al., Isolation, characterization, and localization of heparin-binding growth factors in the heart J. Clin. Invest., 85:433-41, 1990.

Chatterjee et al., Viral gene transfer of the antiapoptotic factor Bcl-2 protects against chronic postischemic heart failure. Circulation, 106 (12 Suppl. 1):I212-1217, 2002.

Chu et al., Toward highly efficient cell-type-specific gene transfer with retroviral vectors displaying single-chain antibodies. J. Virol., 71:720-25, 1997.

Cottrell et al., Silence of the strands: RNA interference in eukaryotic pathogens. Trends Microbiol., 11:37-43,2003; (Abstract Only).

Escobar et al., RNAi-mediated oncogene silencing confers resistance to crown gall tumorigenesis. Proc. Natl. Acad. Sci. USA, 98:13437-42, 2001.

Fefer, "Special delivery" to cancer cells. Blood, 99: 1503-04,2002.

Ghosh et al., Role of superoxide dismutase in survival of Leishrnania within the macrophage. Biochem. J, 369:447-52,2003.

Gussoni et al., Dystrophin expression in the mdx mouse restored by stem cell transplantation. Nature, 401:390-94, 1999 (Abstract only).

Haracska et al., Stimulation of DNA synthesis activity of human DNA polymerase kappa by PCNA Mol. Cell. Biol., 3:784-91,2002.

Hendzel et al., Mitosis-specific phosphorylation of histone H3 initiates primarily within pericentromeric heterochromatin during G2 and spreads in an ordered fashion coincident with mitotic chromosome condensation Chromosoma, 106:348-60, 1997 (Abstract only).

Huser et al Incorporation of decay-accelerating factor into the baculovirus envelope generates complement-resistant gene transfer vectors. Nat. Biotechnol., 19:451-55,2001.

Jackson et al., Mol. Cell. Biol., 7:3709-16, 1990.

Kajstura et al., Telomere Shortening is an in Vivo Marker of Myocyte Replication and Aging Am. J. Pathol., 156:813-19,2000.

Kim et al., Cell cycle regulators during human atrial development Korean J. Intern. Med., 13(2):77-82, 1998; (Abstract).

Kirshenbaum and Schneider, Adenovirus E1A Represses Cardiac Gene Transcription and Reactivates DNA Synthesis in Ventricular Myocytes, via Alternative Pocket Protein- and p300-binding Domains J Biol Chem., 270:7791-94, 1995.

Kwong et al., The suppression of colon cancer cell growth in nude mice by targeting •-catenin/TCF pathway. Oncogene, 21:8340-46, 2002; (abstract only).

Leri et al., Mol. Cell. Cardiol., 3:385-90,2000; (Abstract only).

Liao et al., Cardiac-specific overexpression of cyclin-dependent kinase 2 increases smaller mononuclear cardiomyocytes Circ. Res., 88:443-50,2001.

Lu et al., Polymerizable Fab' antibody fragments for targeting of anticancer drugs. Nat. Biotechnol., 17: 110 1-04, 1999; (Abstract only).

Mastrobattista et al., Functional characterization of an endosome-disruptive peptide and its application in cytosolic delivery of immunoliposome-entrapped proteins. J. Bioi. Chem., 277:27135-43, 2002.

Maxwell and Rivera, Proline oxidase induces apoptosis in tumor cells and its expression is absent or reduced in renal carcinoma. J Biol. Chem., 2003.

Mbugua et al., Cardiotoxicity of Jamesoni's mamba (Dendroaspis jamesoni) venom and its fractionated components in primary cultures of rat myocardial cells in vitro Cell Dev. Biol., 24(8):743-52, 1988.

Neufeld et al., Cell 93:1183-93, 1998 (Abstract only).

Ng et al., An anti-transferrin receptor-avidin fusion protein exhibits both strong proapoptotic activity and the ability to deliver various molecules into cancer cells. Proc. Natl. Acad. Sci.

Nikolaev et al., Parc. A Cytoplasmic Anchor for p53. Cell, 112:29-40,2003.

Oh et al., Telomerase reverse transcriptase promotes cardiac muscle cell proliferation, hypertrophy, and survival Proc. Natl. Acad. Sci., 98(18):10308-313, 2001.

Pagano et al., Cyclin A is required at two points in the human cell cycle EMBO J., 11:961-71, 1992.

Poolman et al., Cell cycle profiles and expressions of p21CIP1 and P27KIP1 during myocyte development Int. J. Cardiol., 67:133-42, 1998 (Abstract only).

Quelle et al., Overexpression of mouse D-type cyclins accelerates G1 phase in rodent fibroblasts Genes Dev., 8:1559-71, 1993 (Abstract only).

Ravnik and Wolgemuth, The developmentally restricted pattern of expression in the male germ line of a murine cyclin A, cyclin A2, suggests roles in both mitotic and meiotic cell cycles Dev. Biol., 173(1):69-78, 1996 (Abstract only).

Reiss et al., Myocardial infarction is coupled with activation of cyclins and cyclin-dependent kinases in myocytes, Exp. Cell Res., 225:44-54, 1996 (Abstract only).

Soonpaa and Field, Survey of studies examining mammalian cardiomyocyte DNA synthesis Circ. Res., 83:15-26, 1998.

Soonpaa et al., Cyclin D1 overexpression promotes cardiomyocyte DNA synthesis and multinucleation in transgenic mice J. Clin. Invest., 99:2644-54, 1997.

Speir et al., Acidic and basic fibroblast growth factors in adult rat heart myocytes. Localization, regulation in culture, and effects on DNA synthesis Circ. Res., 71:251-59, 1992; (Abstract only).

Stein et al., Oligodeoxynucleotides as inhibitors of gene expression: a review. Cancer Res., 48:2659-68, 1998 (Abstract only).

Sweeney et al. A distinct cyclin A is expressed in germ cells in the mouse. Development 1996. vol. 122.

Tang et al., In vivo determination of body composition of rats using magnetic resonance imaging Ann. NY Acad. Sci., 904:32-41, 2000 (Abstract only).

Tavian et al., Stable expression of antisense urokinase mRNA inhibits the proliferation and invasion of human hepatocellular carcinoma cells. Cancer Gene Ther., 10:112-20,2003; (Abstract only).

Wei et al., Inhibition of Rho family GTPases by Rho GDP dissociation inhibitor disrupts cardiac morphogenesis and inhibits cardiomyocyte proliferation. Development, 7: 1705-14, 2002.

Wei et al., Phosphorylation of histone H3 at serine 10 is correlated with chromosome condensation during mitosis and meiosis in Tetrahymena Proc. Natl. Acad. Sci., 95:7480-84, 1998.

Wiesmann et al., Developmental changes of cardiac function and mass assessed with MRI in neonatal, juvenile, and adult mice. Am. J Physiol., 278:H653-57, 2000.

Wilda et al., Killing ofleukemic cells with a BCR/ABL fusion gene RNA interference (RNAi). Oncogene, 21:5716-24,2002, abstract only.

Yoshizumi et al., Disappearance of cyclin A correlates with permanent withdrawal of cardiomyocytes from the cell cycle in human and rat hearts J Clin. Invest., 95:2275-80, 1995.

Zhang et al., An anti-sense construct of full-length AIM cDNA imposes a radiosensitive phenotype on normal cells. Oncogene, 17:811-8, 1998, abstract only.

* cited by examiner

```
  1 mpgtsrhsgr dagsallslh qedqenvnpe klapaqqpra qavlkagnvr gpapqqklkt
 61 rrvaplkdlp indehvtagp swkavskqpa ftihvdeaee tqkrpaelke tecedalafn
121 aavslpaark pltpldypmd gsfesphamd msivledkpv nvnevpdyqe dihtylreme
181 vkckpkvgym krqpditnsm railvdwlve vgeeyklqne tlhlavnyid rflssmsvlr
241 gklqlvgtaa mllaskfeei yppevaefvy itddtyskkq vlrmehlvlk vlafdlaapt
301 vnqfltqyfl hlqpanckve slamflgels lidadpylky lpsliagaaf hlalytvtgq
361 swpeslaqqt gytleslkpc lvdlhqtylk apqhaqqsir ekykhskyhs vsllnppetl
421 sv
```

FIG. 6

C
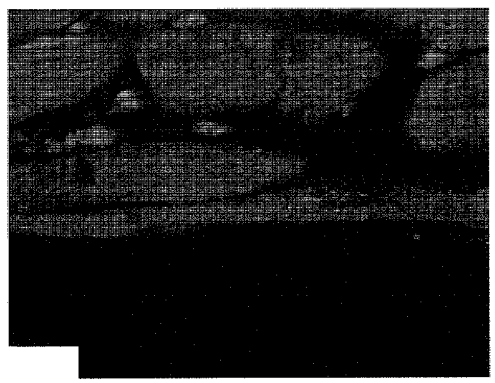
D
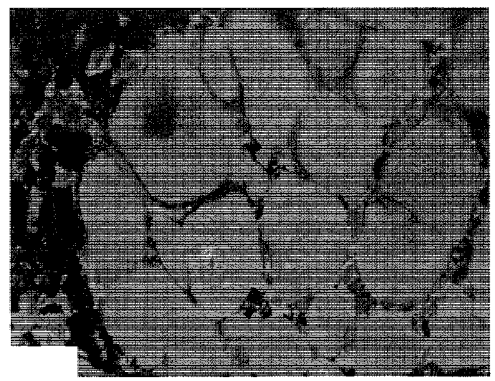
E
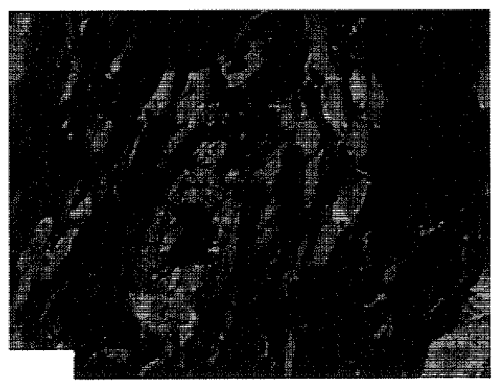
F
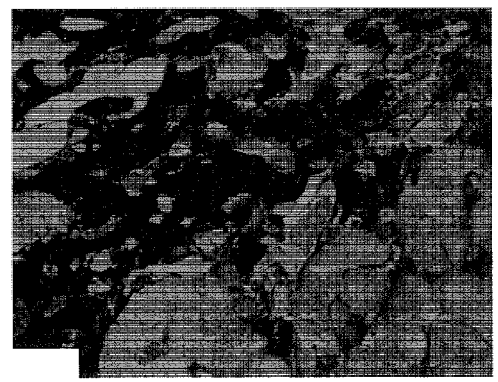
FIG. 12 cont.

COMPOSITIONS AND METHODS FOR TREATING AND PREVENTING HEART TISSUE DEGENERATION, AND USES THEREOF

RELATED APPLICATION

This application claims the benefit of U.S. Provisional Application No. 60/471,952, filed on May 19, 2003.

STATEMENT OF GOVERNMENT INTEREST

This invention was made with government support under Grant No. K08 HL67048-01A1 awarded by National Institutes of Health. The government has certain rights in this invention.

BACKGROUND OF THE INVENTION

Myocardial infarction (irreversible damage to heart tissue, often due to heart attack) is a common life-threatening event that may cause sudden death or heart failure. The ventricular dysfunction that arises after myocardial infarction results, primarily, from a massive loss of cardiomyocytes and gradual replacement of damaged cardiomyocytes with fibrotic non-contractile (scar) tissue. In most cases, the loss of cardiomyocytes after myocardial infarction is irreversible. Indeed, it is widely accepted that the proliferative (and, therefore, the regenerative) potential of adult mammalian cardiomyocytes is quite limited (Rumyantsev and Carlson, *Growth and Hyperplasia of Cardiac Muscle Cells* (New York: Harwood Academic Publishers, 1991)), although this view has recently been challenged (Leri et al., *Mol. Cell. Cardiol.*, 3:385-90, 2000; Kajstura et al., *Am. J. Pathol.*, 156:813-19, 2000; Beltrami et al, *N. Engl. J Med.*, 344(23):1750-57, 2001).

Despite considerable advances in the diagnosis and treatment of heart disease, cardiac damage and dysfunction relating to myocardial infarction are still among the major cardiovascular disorders. Accordingly, it remains a major therapeutic challenge to find new effective approaches to improve cardiac function after myocardial infarction.

The potential to reactivate cardiomyocyte proliferation through the manipulation of putative cellular regulators, or the conversion of pluripotent stem cells to cardiomyocytes (Orlic et al., *Nature*, 410:701-05, 2001), offers an exciting impetus for the design of novel therapeutic interventions to enhance cardiac function during disease conditions. The bulk of evidence obtained over the past decade maintains, however, that mammalian cardiomyocytes proliferate throughout fetal development and into the early neonatal period, at which time DNA replication declines quickly and cell division ceases (Beinlich and Morgan, *Mol. Cell. Biochem.*, 119:3-9, 1993; Casscells et al., *J. Clin. Invest.*, 85:433-41, 1990; Speir et al., *Circ. Res.*, 71:251-59, 1992; Parker and Schneider, *Annu. Rev. Physiol.*, 53:179-200, 1991; Simpson, P. C., *Annu. Rev. Physiol.*, 51:189-202, 1989). Transition from hyperplastic growth (cell division) to hypertrophic growth (increase in cell size) then ensues. In the murine heart, cardiomyocyte division is reportedly completed by birth, with DNA synthesis in neonatal cells (through post-natal day 3) contributing only to binucleation (Soonpaa et al., *J. Mol. Cell. Cardiol.*, 28:1737-46, 1996). The cessation of myocyte proliferation is attributed to an arrest of the cell cycle (Brooks et al., *Cardiovasc. Res.*, 39:301-11, 1998). In accordance with this hypothesis, adult rat cardiomyocytes have been shown to display a dual cell-cycle blockade, with approximately 80% of cells arresting in G0/G1, and 15% -20% of cells arresting in G2/M (Poolman and Brooks, *Mol. Cell. Cardiol.*, 29:A19 (Abstract), 1997; Poolman et al., *Int. J. Cardiol.*, 67:133-42, 1998).

Progression through the cell cycle is tightly regulated, and involves cyclins complexed with their catalytic partners, the cyclin-dependent kinases (cdks). Among the cyclins, cyclin A2 is unique in that it regulates progression through two critical transitions: cyclin A2 complexed with cdk2 is essential for the G1/S transition, and cyclin A2 complexed with cdk1 promotes entry into mitosis (Sherr and Roberts, *Genes Dev.*, 9:1149-63, 1995; Pagano et al., *EMBO J.*, 11:961-71, 1992). It is well-established that mammalian cardiomyocytes cease to proliferate in the early neonatal period due to arrest of the cell cycle. Cyclin A2 is the only cyclin to be completely downregulated, at both the message and protein level, during cardiogenesis, in rat and human, in a manner that appears coincident with this withdrawal of cardiomyocytes from the cell cycle (Yoshizumi et al., *J. Clin. Invest.*, 95:2275-80, 1995).

Previously, it has been shown that zebrafish fully regenerate hearts within 2 months of 20% ventricular resection, due to robust proliferation of cardiomyocytes localized at the leading epicardial edge of the new myocardium. This injury-induced cardiomyocyte proliferation was able to overcome scar formation, allowing cardiac muscle regeneration. It has been suggested that this regeneration of heart tissue in zebrafish is related to the Mps1 mitotic checkpoint kinase (Poss et al., Heart regeneration in zebrafish. *Science*, 298:2188-90, 2002). It has also been shown that cardiomyocytes react to myocardial infarction by activating cyclins and cyclin-dependent kinases (Reiss et al., Myocardial infarction is coupled with activation of cyclins and cyclin-dependent kinases in myocytes, *Exp. Cell Res.*, 225:44-54, 1996). However, prior to the present invention, it had not been directly demonstrated that regulation of cyclins, particularly cyclin A2, can induce cardiomyocyte mitosis once the timeline for cell-cycle exit (and, therefore, "terminal" differentiation) has been surpassed.

SUMMARY OF THE INVENTION

The inventors hypothesized that downregulation of cyclin A2 plays a crucial role in cardiomyocyte cell-cycle exit, and that, conversely, the continued expression of cyclin A2 in the heart results in altered cell division and, importantly, cardiomyocyte hyperplasia. To determine whether the stimulation of myocyte mitotic divisions would have an impact upon cardiomyocyte cell-cycle withdrawal, the inventors created a cardiac-specific cyclin A2 transgenic mouse model which constitutively expresses cyclin A2 in the cardiomyocyte lineage, from embryogenesis through adulthood. This model was previously shown to exhibit cardiomyocyte mitosis in differentiated cardiomyocytes. The inventors now show that the presence in the heart of cyclin A2—a protein that is normally silenced in the postnatal heart (and absent after birth) in mice, rats, and humans—prevents myocardial injury that is induced by ligation of the left anterior descending coronary artery.

In particular, the inventors have observed that regeneration of healthy myocardium occurs within 2 weeks after myocardial infarction in cyclin A2 transgenic animals, but not in control animals. Cyclin A2 induced cardiac enlargement in the transgenic animals, due to cardiomyocyte hyperplasia, when constitutively expressed from embryonic day 8 into adulthood. This hyperplasia was correlated with an increase in cardiomyocyte mitoses through post-natal development.

The inventors' model represents an improvement over existing techniques for preventing and treating myocardial injury in that it utilizes an endogenous cell-cycle regulator, it induces native cardiomyocytes to regenerate, and it does not require introduction of another cell type (e.g., a stem cell) that may not fully acquire the characteristics of cardiomyocytes.

Accordingly, the present invention provides a method for promoting generation of heart tissue, by augmenting cyclin in heart tissue cells or in side-population (SP) progenitor cells. The present invention further provides a method for preventing degeneration of heart tissue, by augmenting cyclin in cells of the heart tissue.

The present invention also provides a method for treating heart tissue degeneration in a subject, including the steps of: (a) obtaining or generating a population of cells selected from heart tissue cells, side-population (SP) progenitor cells, and stem cells; (b) augmenting cyclin in the cells; and (c) transplanting the cells containing augmented cyclin, and their progeny, if any, into the subject, in amounts effective to treat the heart tissue degeneration.

Further provided is a method for treating or preventing heart tissue degeneration in a subject, by administering to the subject an amount of a cyclin-associated agent effective to treat or prevent heart tissue degeneration.

Additionally, the present invention provides a therapeutic composition, including: (a) a cyclin-associated agent; and (b) optionally, a pharmaceutically-acceptable carrier. Also provided is a kit for use in delivering a cyclin-associated agent to heart tissue cells, side-population (SP) progenitor cells, or stem cells, that includes the therapeutic composition and a catheter.

The present invention further provides a heart tissue cell, side-population (SP) progenitor cell, or stem cell in which cyclin A2 is augmented. Also provided are cell lines comprising these cells, and in vitro and in vivo screening methods using the cell lines.

The present invention further provides an in vitro method for screening for at least one cardiotoxic effect in a candidate drug that is potentially useful for the treatment of a pediatric disorder, including the steps of: (a) contacting at least one heart tissue cell in which cyclin A2 is augmented with a candidate drug that is potentially useful for the treatment of a pediatric disorder; and (b) assaying the at least one heart tissue cell for at least one cardiotoxic effect. Also provided is a drug screened by this method.

Furthermore, the present invention provides an in vitro method for screening a candidate agent for synergy with cyclin in the treatment or prevention of heart tissue degeneration, including the steps of: (a) contacting at least one heart tissue cell in which cyclin A2 is augmented with a candidate agent; and (b) assessing the ability of the candidate agent to enhance heart tissue generation. Also provided is an agent identified by this method, and a method for treating or preventing heart tissue degeneration in a subject by administering this agent to the subject, in combination with a cyclin-associated agent, in amounts effective to treat or prevent heart tissue degeneration.

Additionally, the present invention provides an in vivo method for screening a candidate agent for synergy with cyclin in the treatment or prevention of heart tissue degeneration, including the steps of: (a) contacting heart tissue cells in which cyclin A2 is augmented with a candidate agent; (b) transplanting the heart tissue cells and their progeny, if any, into a subject; and (c) assessing the ability of the candidate agent to enhance survival of the heart tissue cells and progeny thereof after transplantation. Also provided is an agent identified by this method, and a method for treating or preventing heart tissue degeneration in a subject by administering this agent to the subject, in combination with a cyclin-associated agent, in amounts effective to treat or prevent heart tissue degeneration.

The present invention also provides an in vitro method for screening for a candidate drug that has at least one toxic effect on stem cells, wherein the toxic effect is prevented or attenuated in the presence of augmented cyclin, by: (a) contacting stem cells of the stem cell line of the present invention with a candidate drug; (b) contacting control stem cells, that do not have augmented cyclin, with the candidate drug; and (c) assaying the stem cells of step (a) and the control stem cells of step (b) for at least one toxic effect, wherein the presence of a toxic effect in the control stem cells of step (b), but an absent, or attenuated, toxic effect in the stem cells of step (a), is indicative that the candidate drug has at least one toxic effect on stem cells, wherein the toxic effect is prevented or attenuated in the presence of augmented cyclin. Also provided is a drug screened by this method.

The present invention further provides an in vitro system for use in screening for at least one cardiotoxic effect in a candidate drug that is potentially useful for the treatment of a pediatric disorder, comprising a population of heart tissue cells in which cyclin A2 is augmented.

The present invention also provides an in vitro system for use in screening a candidate agent for synergy with cyclin in the treatment or prevention of heart tissue degeneration, comprising a population of heart tissue cells in which cyclin A2 is augmented.

Further provided is an in vitro system for use in screening for a candidate drug that has at least one toxic effect on stem cells, wherein the toxic effect is prevented or attenuated in the presence of augmented cyclin, comprising a population of stem cells in which cyclin A2 is augmented.

Additionally, the present invention provides a use of a cyclin-associated agent in the generation of heart tissue.

Finally, the present invention provides a use of a cyclin-associated agent in the treatment or prevention of heart tissue degeneration.

Additional aspects of the present invention will be apparent in view of the description which follows.

BRIEF DESCRIPTION OF THE FIGURES

FIG. 6 sets forth the amino acid sequence of mouse cyclin A2 (SEQ ID NO:1).

DETAILED DESCRIPTION OF THE INVENTION

Figure 1:
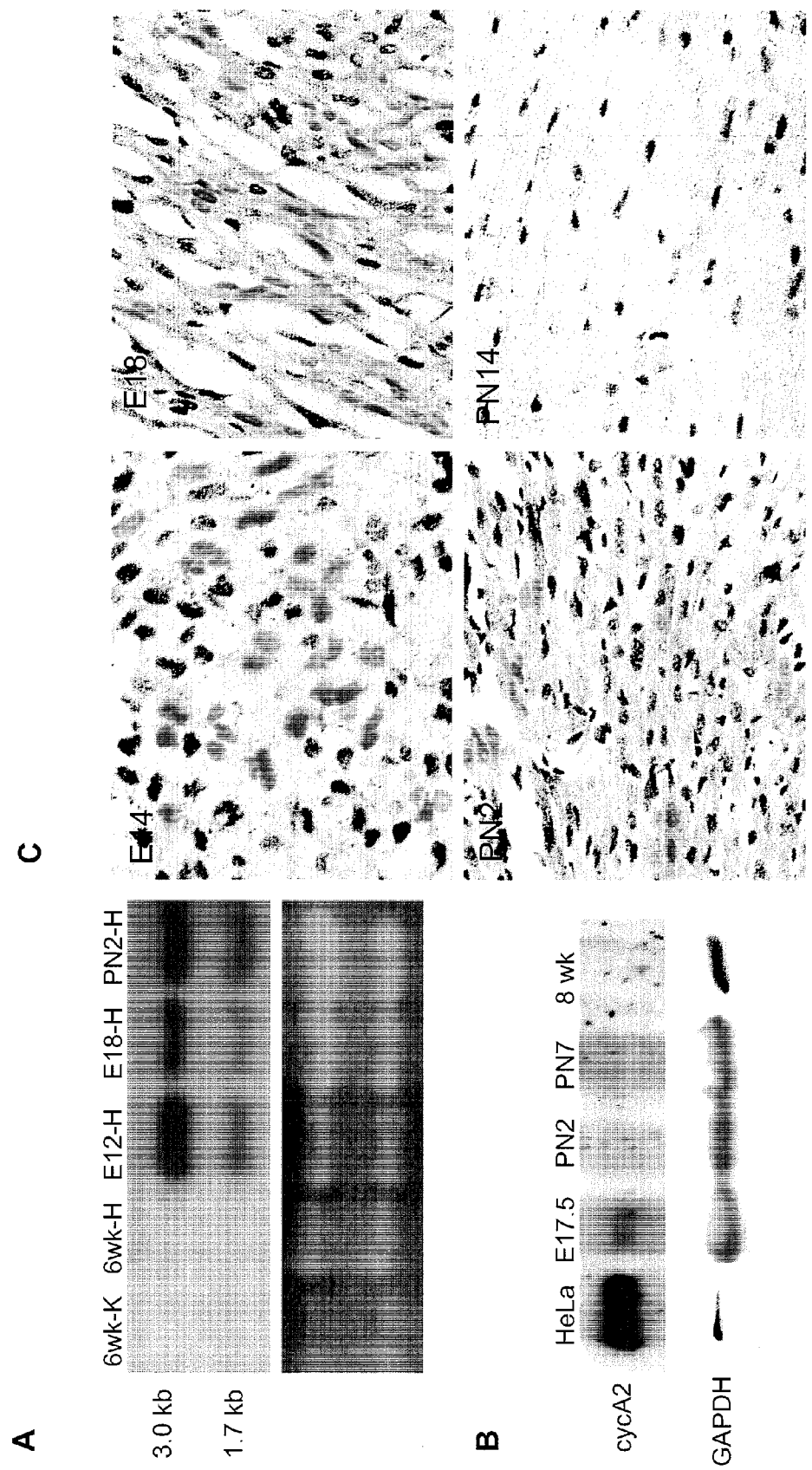
FIG. 1 shows that cyclin A2 mRNA and protein expression are developmentally regulated in the normal mouse heart. (A) Cyclin A2 mRNA expression in normal mouse hearts was detected by Northern-blot analysis. RNA was extracted from the following tissues: 6-week heart (HA), 6-week kidney (KA), E12 heart (HE12), E18 heart (HE18), and PN2 heart (HPN2). The ethidium-bromide-stained ribosomal RNA bands are shown in the bottom panel as a loading control. (B) Immunoblot analysis of cyclin A2 protein expression in normal mouse. Protein was extracted from mouse hearts at E17.5, PN2, PN7, and 8 weeks of age (labeled 'adult'), electrophoresed on 10% PAGE, and detected by α-cyclin A2 antibody (top). α-GAPDH antibody was used as a control for equivalent loading. (C) Cellular localization of cyclin A2 protein expression in the developing heart. Immuno-histochemical staining utilizing α-cyclin A2 antibody in ventricular tissue sections from selected stages (embryonic day 14 (E14) through post-natal day 14 (PN14)). The brown staining indicates positively-stained cardiomyocyte nuclei.

Genetic modulation, cell transplantation, and tissue engineering promise revolutionary approaches for myocardial regeneration and tissue repair after myocardial injury. Current data derived from animal models suggest that it may be possible to treat heart failure by inserting genetic materials or myogenic cells into injured myocardium. See, e.g., U.S. Pat. No. 6,534,052 and U.S. Patent Applications Nos. 20030022367, 20030054973, and 20020197240.

One possible approach to cardiac regeneration involves manipulation of cellular proteins to promote cell-cycle re-entry and proliferation of cardiomyocytes. This approach has received considerable interest in recent years, due to the identification of key cell-cycle regulatory proteins and the publication of several reports suggesting that manipulation of these factors can reactivate DNA synthesis in vivo and in vitro in the post-mitotic ventricular myocardium (Kirshenbaum and Schneider, *J. Biol. Chem.*, 270:7791-94, 1995; Agah et al., *J. Clin. Invest.*, 100:2722-28, 1997; Soonpaa and Field, *Circ. Res.*, 83:15-26, 1998). Prior to the present invention, however, no previous report directly demonstrated that regulation of these factors can induce cardiomyocyte mitosis once the timeline for cell-cycle exit (and, therefore, terminal differentiation) has been surpassed.

Previously, a significant gap in understanding of the cardiomyocyte cell cycle resulted from the limited number of studies that explore the effects of putative cellular regulators of the G2/M checkpoint. Cyclin A2 is unique among all cyclins in that it has been shown to regulate transition through both G1/S and G2/M phases in cultured cell lines (Sherr and Roberts, *Genes Dev.*, 9:1149-63, 1995). Cyclin A2 is normally silenced in the heart shortly after birth, when cardiomyocyte division ceases as the cells withdraw from the cell cycle. This was previously established in rat and human hearts (Yoshizumi et al., *J. Clin. Invest.*, 95:2275-80, 1995), and the inventors have confirmed this in the mouse. The temporal pattern of cyclin A2 mRNA and protein levels implicates a crucial role for cyclin A2 as a regulator of cardiomyocyte cell-cycle exit.

To further elucidate the cardiomyocyte cell cycle, the inventors generated a mouse model of constitutive cyclin A2 expression in the myocardium, and tested the impact of deregulated cyclin A2 expression on cardiomyocyte proliferation and terminal differentiation. Phenotypic analysis revealed cardiac enlargement due to hyperplasia in the adult heart. More importantly, cardiomyocyte mitoses were significantly enhanced during post-natal development in the transgenic hearts, as compared with normal hearts, with the most dramatic difference occurring at PN7. However, cardiac enlargement in the transgenic mice became statistically significant during adulthood at 6 months of age, implying that the hyperplasia induced by constitutive cyclin A2 expression arose primarily during post-natal development, and not during embryogenesis.

Earlier studies had suggested that embryogenesis was responsible for hyperplasia in several other mouse models of altered or absent cell-cycle proteins. For example, Liao et al. (*Circ. Res.*, 88:443-50, 2001) noted that cardiac overexpression of cdk2 elicited cardiac enlargement at PN2, but that this did not persist in adults. The cardiac phenotype of p27$^{KIP1}$ knockout mice exhibited a significant increase in heart weight, when compared with wild-type, as analyzed between 2 and 35 days of age (Poolman et al., *Circ. Res.*, 85:117-27, 1999). C-myc-overexpressing mice exhibited an enlargement in cardiac size that was most profound at 1 and 15 days of age (44% and 46%, respectively); however, by 60 days of age, only a 34% increase was noted (Jackson et al., *Mol. Cell. Biol.*, 7:3709-16, 1990). In all of these studies, the investigators concluded that this hyperplasia occurred during fetal development, without acceleration of post-natal growth.

Cyclin D1 overexpression in the mouse heart has been shown to promote increased DNA synthesis in adult transgenic hearts, resulting in multinucleation; karyokinesis was not noted (Soonpaa et al., *J. Clin. Invest.*, 99:2644-54, 1997). Approximately 40% enlargement was noted when the HW/BW ratios of adult transgenic mice were compared with those of non-transgenic mice (n=4 for each group, age not specified). Although >60% of the adult cyclin D1 transgenic cardiomyocytes exhibited a multinucleated phenotype, the authors concluded that it was unclear whether these cardiomyocytes retained the ability to undergo karyokinesis. This same group of investigators had previously demonstrated (Soonpaa et al., *J. Clin. Invest.*, 99:2644-54, 1997) that cardiomyocyte division in the normal mouse heart does not occur after birth, with DNA synthesis through PN2 and PN3 contributing only to binucleation.

The inventors' model of constitutive cardiac cyclin A2 expression directly demonstrates that karyokinesis is induced in the transgenic heart after birth. A recently-published report, describing the effect of inhibition of the Rho family GTPases, lends further support to the association of cyclin A2 and cardiomyocyte proliferation: expression of Rho GDIα, an inhibitor of Rho family proteins, in the mouse myocardium resulted in a decrease in cellular proliferation in the embryonic heart that was associated with downregulation of cyclin A (Wei et al., *Development*, 7:1705-14, 2002).

As cyclin A2 has been shown to regulate both G1/S and G2/M in cultured mammalian cell lines (Sherr and Roberts, *Genes Dev.*, 9:1149-63, 1995), the inventors presumed that it plays a role in the regulation of both gap phases in vivo. In *Drosophila*, when regulators of both gap phases are overproduced (i.e., cyclin E and string), cells are unable to compensate for the shortening of both gap phases; the cell cycle as a whole is abbreviated, resulting in small cells with a faster generation time (Neufeld et al., *Cell*, 93:1183-93, 1998). Previous investigators have demonstrated that overexpression of G1- to S-phase cell-cycle regulatory proteins decreased cell size in vitro and in vivo (Liao et al., *Circ. Res.*, 88:443-50, 2001; Quelle et al., *Genes Dev.*, 8:1559-71, 1993). This mechanism may account, in part, for the cardiomyocyte hyperplasia with smaller cells that was noted in the inventors' model. However, the lack of any significant cardiac enlargement in the inventors' model during post-natal development, with an age-related increase in the cardiac size gap between transgenic and normal animals, points to the conclusion that the most dramatic effect of "de-silencing" cyclin A2 occurs after birth, when cardiogenesis is normally complete.

In order to test whether cyclin A2 can contribute to cardiac repair, the inventors induced myocardial infarction (MI) in transgenic mice, non-transgenic littermates, and wild-type mice (strain and age-matched) via ligation of the left anterior descending artery (LAD). In total, 89 mice were infarcted; there was an 83% survival rate, 1 week post-MI.

Functional analysis was performed utilizing fMRI to measure volumetric ejection fraction (EF); tagging was used to determine regional wall motion. Cyclin A2 transgenic mice displayed markedly-enhanced EF, as compared with controls, at 3 weeks and 3 months post-MI. The percent of left ventricle (LV) infarcted was consistent among all groups. In the transgenic hearts, preservation of cardiac function was observed at 3 months of age, with a decline in EF and fractional shortening noted at 8 months of age. This is consistent with the observation of greater HW/BW differences between transgenic and normal animals after 5-6 months of age, as compared with younger animals. It is expected that hyperplastic hearts will display hypercontractility that will ultimately progress to hypocontractility with age.

The inventors also examined potential cellular and molecular mechanisms that may contribute to the apparent recovery of cardiac function. Assays of proliferation included immunofluorescence and confocal microscopy to detect phospho-histone H3 (H3P), a mitosis-specific marker. BRDU labeling was also performed. In these studies, the inventors found mitotic nuclei (as assessed by immunostaining for anti-phosphohistone H3) that were localized to cardiomyocytes in the infarct zone and in non-infarcted myocardium in transgenic mice; only 0-1 such mitosis was noted in non-transgenic and wild-type hearts. This suggests that cyclin A2 transgenic cardiomyocytes are able to re-enter the cell cycle in response to injury.

Cardiac progenitor cells were detected in the infarct zones of both transgenic animals and controls. These progenitor cells express ABCG2, a known marker of "side-population" (SP) cells. SP cells form a class of progenitor cells that are identified on the basis of Hoechst extrusion. They have been observed on many tissues, including skeletal muscle, bone marrow, liver, brain, and heart. In transgenic hearts alone, nuclear localization of cyclin A2 was detected in what appears to be "de novo" myocardium. These results indicate that cyclin A2 transgenic mice are able to repair damaged myocardium either through cell-cycle re-entry of peri-infarct zone cardiomyocytes or via the induction of SP cells with enhanced proliferative potential.

The expression of cyclin A2 in the nucleus of what appears to be "de novo" myocardium recapitulates the developmental paradigm noted in the post-natal transgenic model. The presence of nuclear cyclin A2, coupled with the findings of ABCG2 expression in cells of similar location (as serial sections were analyzed), implies that the SP cells of the transgenic model, which normally reside in myocardium, exhibit a "hyperproliferative" phenotype. This may have exciting ramifications for cardiac regeneration.

In the inventors' transgenic model, then, constitutive cardiac expression of normally-silent cyclin A2 invoked an increase in cardiomyocyte mitosis in the post-natal heart, with resultant cardiac enlargement (due to hyperplasia) noted in the adult heart. The inventors' model differs from previous mouse models examining altered or absent cell-cycle regulators in that it specifically addresses control of the G2/M checkpoint, in addition to the G1/S checkpoint. Furthermore, karyokinesis in post-natal cardiomyocytes is specifically demonstrated through the detection of histone-3 phosphorylation at Ser10, and various stages of cardiomyocyte mitosis may be observed. The enhanced HW/BW increase in the transgenic heart, as compared with the normal heart during adulthood, suggests that cytokinesis is coupled with mitosis in the transgenic heart. The decline of cardiomyocyte mitoses noted between PN7 and PN14, and the scattered mitoses noted in the adult heart, indicate that cell cycle inhibitors are holding this mitotic process in check, despite the expression of cyclin A2.

Moreover, cyclin A2 transgenic mice have significantly enhanced cardiac function compared to non-transgenic littermates and wild-type controls at 3 weeks and 3 months post-MI. This suggests that cyclin A2 may confer the ability to re-enter the cell cycle for post-mitotic cardiomyocytes. Cyclin A2 also appears to confer a hyperproliferative effect on side-population progenitor cells that are normally found in myocardium.

In view of the foregoing, the present invention provides a method for promoting generation of heart tissue. As used herein, the term "promoting generation of heart tissue" includes activating, enhancing, facilitating, increasing, inducing, initiating, or stimulating the growth and/or proliferation of heart tissue, as well as activating, enhancing, facilitating, increasing, inducing, initiating, or stimulating the differentiation, growth, and/or proliferation of heart tissue cells. Thus, the term includes initiation of heart tissue generation, as well as facilitation or enhancement of heart tissue generation already in progress. "Differentiation" is the cellular process by which cells become structurally and functionally specialized during development. The terms "proliferation" and "growth", as used herein, refer to an increase in mass, volume, and/or thickness of heart tissue, as well as an increase in diameter, mass, or number of heart tissue cells. As further used herein, the term "generation" includes the generation of new heart tissue and the regeneration of heart tissue where heart tissue previously existed.

As used herein, the term "heart tissue" includes, without limitation, the myocardium of the heart (including cardiac muscle fibers, connective tissue (endomysium), nerve fibers, capillaries, and lymphatics); the endocardium of the heart (including endothelium, connective tissue, and fat cells); the epicardium of the heart (including fibroelastic connective tissue, blood vessels, lymphatics, nerve fibers, fat tissue, and a mesothelial membrane consisting of squamous epithelial cells); and any additional connective tissue (including the pericardium), blood vessels, lymphatics, fat cells, progenitor cells (e.g., side-population (SP) progenitor cells), and nervous tissue found in the heart. Cardiac muscle fibers are composed of chains of contiguous heart-muscle cells, or "cardiomyocytes", joined end to end at intercalated disks. These disks possess two kinds of cell junctions: expanded desmosomes extending along their transverse portions, and gap junctions, the largest of which lie along their longitudinal portions.

The method of the present invention comprises, in one embodiment, augmenting cyclin in heart tissue cells. Heart tissue cells include any of the cells of the various tissues found in the heart, as described above. By way of example, the heart tissue cells of the present invention may include progenitor cells (e.g., heart-tissue side-population (SP) progenitor cells) and differentiated or post-mitotic cells. The term "post-mitotic", as used herein, refers to a cell that is in G0 phase (a quiescent state), and is no longer dividing or cycling. In a preferred embodiment of the present invention, the heart tissue cells are cardiomyocytes. It is also within the confines of the present invention that generation of heart tissue may be promoted by augmenting cyclin in SP progenitor cells that are derived from non-heart tissue (e.g., spleen, bone marrow, skeletal muscle, brain, liver, kidney, lung, small intestine, etc.).

The heart tissue cells and SP progenitor cells of the present invention may be obtained from any animal, including amphibians, birds, fish, mammals, and marsupials, but are preferably obtained from a mammal (e.g., a human; a domestic animal, such as a cat, dog, monkey, mouse, and rat; or a commercial animal, such as a cow or pig). Additionally, the heart tissue cells and SP progenitor cells of the present invention may be obtained from an animal of any age, including a fetus, an embryo, a child, and an adult. In one embodiment of the present invention, the heart tissue cells or SP progenitor cells are obtained from a transgenic animal that overexpresses cyclin A2 in its heart tissue, as described below. In another embodiment, the heart tissue cells or SP progenitor cells are rat or mouse cells. In a preferred embodiment of the present invention, the heart tissue cells or SP progenitor cells are obtained from a human.

As described above, the method of the present invention results in the generation of new heart tissue and/or the regeneration of heart tissue where such tissue used to exist. In the case of regeneration, the heart tissue cells of the present invention may be obtained from, or found within, damaged or degenerated heart tissue (i.e., heart tissue which exhibits a pathological condition). Causes of heart tissue degeneration include, without limitation, chronic heart damage, chronic heart failure, damage resulting from injury or trauma, damage resulting from a cardiotoxin, damage from radiation or oxidative free radicals, damage resulting from decreased blood flow, and myocardial infarction (such as a heart attack). Preferably, the degenerated heart tissue of the present invention results from a myocardial infarction or heart failure. Generation of new heart tissue and regeneration of heart tissue may be measured or detected by known procedures, including Western blotting for heart-specific proteins, electron microscopy in conjunction with morphometry, simple assays to measure rate of cell proliferation (including trypan blue staining, the CellTiter-Blue cell viability assay from Promega (Madison, Wis.), the MTT cell proliferation assay from ATCC, differential staining with fluorescein diacetate and ethidium bromide/propidium iodide, estimation of ATP levels, flow-cytometry assays, etc.), and any of the methods, molecular procedures, and assays disclosed herein.

As discussed above, cyclin is augmented in heart tissue cells or SP progenitor cells in accordance with the method of the present invention. Cyclins are proteins, found in certain eukaryotic cells, which help to regulate the cell cycle by causing cells to begin mitosis (a form of nuclear division). The proteins are generally produced during all parts of the cell cycle, but destroyed during mitosis. Examples of cyclins include, without limitation, cyclin A, cyclin B, cyclin C, cyclin D, and cyclin E. The mammalian A-type cyclin family consists of 2 members, cyclin A1 (the germ-cell version of cyclin A) and cyclin A2 (the somatic-cell version of cyclin A, known as "cyclin A" in humans). Included in this family is a 33-kD protein identical to adenovirus e1a-associated protein p60. Cyclin A proteins regulate p33cdk2 and p34cdc2, and are necessary for progression through the S phase of the cell cycle. Cyclin A2 promotes both G1/S and G2/M transitions; cyclin A1 is expressed in mice exclusively in the germline lineage, and is expressed in humans at highest levels in the testis and certain myeloid leukemia cells. Cyclin B is a 58-kD protein that is regulated post-transcriptionally and post-translationally in the cell cycle. In one preferred embodiment of the present invention, the cyclin is cyclin A2.

As used herein, "cyclin" includes both a "cyclin protein" and a "cyclin analogue". Unless otherwise indicated, "protein" shall include a protein, protein domain, polypeptide, or peptide, and any fragment or variant thereof having protein function. The variants preferably have greater than about 75% homology with the naturally-occurring protein sequence, more preferably have greater than about 80% homology, even more preferably have greater than about 85% homology, and, most preferably, have greater than about 90% homology with the protein sequence. In some embodiments, the homology may be as high as about 93-95%, 98%, or 99%. These variants maybe substitutional, insertional, or deletional variants. The variants may also be chemically-modified derivatives: proteins which have been subjected to chemical modification, but which retain the biological characteristics of the naturally-occurring protein. In one embodiment of the present invention, the protein is mutated such that it has a longer half-life inside the heart tissue cell (e.g., it is modified at its ubiquitin-binding site).

A "cyclin analogue", as used herein, is a functional variant of the cyclin protein, having cyclin biological activity, that has 60% or greater (preferably, 70% or greater) amino-acid-sequence homology with the cyclin protein. As further used herein, the term "cyclin biological activity" refers to the activity of a protein or peptide that demonstrates an ability to promote generation of heart tissue, as described herein.

The cyclin A2 protein has the amino acid sequence set forth in FIG. 6, including conservative substitutions thereof. As used herein, "conservative substitutions" are those amino acid substitutions which are functionally equivalent to a substituted amino acid residue, either because they have similar polarity or steric arrangement, or because they belong to the same class as the substituted residue (e.g., hydrophobic, acidic, or basic). The term "conservative substitutions" includes substitutions having an inconsequential effect on the ability of cyclin to promote generation of heart tissue, particularly in respect of the use of said interaction for the identification and design of agonists of cyclin, for molecular replacement analyses, and/or for homology modeling.

It will be obvious to the skilled practitioner that the numbering of amino acid residues in proteins, and in the fragments, variants, analogues, and peptidomimetics covered by the present invention, may be different than that set forth herein, or may contain certain conservative amino acid substitutions that produce the same heart-tissue-generating activity as that described herein. Corresponding amino acids and conservative substitutions in other isoforms or analogues are easily identified by visually inspecting the relevant amino acid sequences, or by using commercially-available homology software programs.

In accordance with methods described herein, cyclin may be augmented or increased in heart tissue cells or side-population (SP) progenitor cells by activating, facilitating, inducing, or stimulating one or more functions, activities, or effects (e.g., downstream effects of the cyclin in the cyclin signal transduction pathway) of cyclin in the cells, particularly those that result in promotion of heart-tissue generation, or by increasing the amount, expression, or level of cyclin in the cells. Furthermore, one or more cyclin functions, activities, effects, expression, and levels in a cell may be augmented by targeting cyclin directly, or by targeting cyclin indirectly, via an enzyme or other endogenous molecule that regulates or modulates the functions, activities, effects, expression, and/or levels of cyclin in the cell. Cyclin expression may also be augmented by engineering the cyclin gene so that cyclin is expressed on an inducible promoter. In such a case, cyclin expression would be sustained in the presence of a suitable inducing agent, but would shut down once the supply of inducer was depleted, thereby bringing about a decrease in the amount or level of cyclin in the cell. Cyclin also may be augmented in a cell by activating, facilitating, inducing, or stimulating the functions, activities, effects, expression, and levels of endogenous cyclin, or by introduction of an exogenous cyclin, particularly where the cyclin is under the control of a strong promoter.

Preferably, the functions, activities, effects, expression, and/or levels of cyclin in the heart tissue cells of the present invention are augmented or increased by at least 10%. More preferably, the functions, activities, effects, expression, and/ or levels of the cyclin are increased by at least 20%. The functions, activities, effects, expression, and/or levels of cyclin are augmented in heart tissue cells or side-population (SP) progenitor cells by an amount effective to promote generation of heart tissue. This amount may be readily determined by the skilled artisan, based upon known procedures, including analysis of titration curves established in vivo, methods disclosed herein, and techniques known to one of skill in the art.

In the method of the present invention, the functions, activities, effects, expression, and/or levels of cyclin in heart tissue cells or side-population (SP) progenitor cells are preferably augmented by contacting the cells (i.e., treating the cells) with a cyclin-associated agent. As used herein, an "agent" shall include a protein, polypeptide, peptide, nucleic acid (including DNA, RNA, and an antisense oligonucleotide), antibody (monoclonal and polyclonal), Fab fragment, $F(ab')_2$ fragment, molecule, compound, antibiotic, drug, and any combinations thereof, and may be an agent reactive with cyclin. The term "reactive", as used herein, means that the molecule or mimetic has affinity for, binds to, or is directed against cyclin. A Fab fragment is a univalent antigen-binding fragment of an antibody, which is produced by papain digestion. A $F(ab')_2$ fragment is a divalent antigen-binding fragment of an antibody, which is produced by pepsin digestion.

As further used herein, the term "cyclin-associated agent" includes a cyclin protein, including an exogenous cyclin protein; a cyclin nucleic acid (i.e., a nucleic acid encoding a cyclin); a member of a cyclin signal-transduction pathway (including upstream and downstream effectors and activators, in either protein or nucleic acid form); and a modulator (e.g., inhibitor, activator, antagonist, or agonist) of a member of the cyclin signal-transduction pathway or system (i.e., a modulator which affects the expression, activity, function, and/or effect of a member of the cyclin signal-transduction pathway), in either protein or nucleic acid form, including a modulator of cyclin expression. Additionally, as used herein, a "member of a cyclin signal-transduction pathway" includes a downstream effector or an upstream regulator of cyclin in heart tissue cells or side-population (SP) progenitor cells.

By way of example, activity of cyclin in heart tissue cells or side-population (SP) progenitor cells may be augmented by contacting the cells with a small molecule or protein mimetic that stimulates cyclin activity and/or that is reactive with cyclin. Similarly, the level of cyclin in heart tissue cells or side-population (SP) progenitor cells may be augmented by directly or indirectly causing, inducing, or stimulating the upregulation of cyclin expression within a subject. Accordingly, in one embodiment of the present invention, activity of cyclin is increased in a subject by administering to the subject a modulator of cyclin expression.

In one embodiment of the present invention, the cyclin-associated agent is a protein. Examples of proteins for use in the present invention include, without limitation, cyclin proteins, members of the cyclin signal-transduction pathway (including upstream and downstream effector and activator polypeptides), modulators (e.g., inhibitors, activators, antagonists, or agonists) of a member of the cyclin signal-transduction pathway/system, cyclin-associated antibodies (e.g., IgA, IgD, IgE, IgG, IgM, single-chain antibodies, and Fab' fragments, such as scFv) that are capable of binding and inhibiting a negative regulator of the cyclin signal-transduction pathway, and cyclin-associated ligands (e.g., a ligand for a member of the cyclin signal-transduction pathway, and derivatives thereof). Preferably, the cyclin-associated protein is cyclin A2 protein.

Where the protein of the present invention is an antibody, the protein is preferably a mammalian antibody (e.g., a human antibody) or a chimeric antibody (e.g., a humanized antibody). More preferably, the antibody is a human or humanized antibody. As used herein, the term "humanized antibody" refers to a genetically-engineered antibody in which the minimum portion of an animal antibody (e.g., an antibody of a mouse, rat, pig, goat, or chicken) that is generally essential for its specific functions is "fused" onto a human antibody. In general, a humanized antibody is 1-25%, preferably 5-10%, animal; the remainder is human. Humanized antibodies usually initiate minimal or no response in the human immune system. Methods for expressing fully human or humanized antibodies in organisms other than human are well known in the art: see, e.g., U.S. Pat. No. 6,150,584, Human antibodies derived from immunized xenomice; U.S. Pat. No. 6,162,963, Generation of xenogenetic antibodies; and U.S. Pat. No. 6,479,284, Humanized antibody and uses thereof In one embodiment of the present invention, the antibody is a single-chain antibody. In a preferred embodiment, the single-chain antibody is a human or humanized single-chain antibody. In another preferred embodiment of the present invention, the antibody is a murine antibody.

The cyclin-associated agent of the present invention may also be a nucleic acid. As used herein, a "nucleic acid" or "polynucleotide" includes a nucleic acid, an oligonucleotide, a nucleotide, a polynucleotide, and any fragment or variant thereof. The nucleic acid or polynucleotide may be double-stranded, single-stranded, or triple-stranded DNA or RNA (including cDNA), or a DNA-RNA hybrid of genetic or synthetic origin, wherein the nucleic acid contains any combination of deoxyribonucleotides and ribonucleotides and any combination of bases, including, but not limited to, adenine, thymine, cytosine, guanine, uracil, inosine, and xanthine hypoxanthine. The nucleic acid or polynucleotide may be combined with a carbohydrate, a lipid, a protein, or other materials. Preferably, the nucleic acid encodes cyclin A2 protein.

The "complement" of a nucleic acid refers, herein, to a nucleic acid molecule which is completely complementary to another nucleic acid, or which will hybridize to the other nucleic acid under conditions of high stringency. High-stringency conditions are known in the art: see, e.g., Maniatis et al., *Molecular Cloning. A Laboratory Manual*, 2nd ed. (Cold Spring Harbor: Cold Spring Harbor Laboratory, 1989) and Ausubel et al., eds., *Current Protocols in Molecular Biology* (New York, N.Y.: John Wiley & Sons, Inc., 2001). Stringent conditions are sequence-dependent, and may vary depending upon the circumstances. As used herein, the term "cDNA" refers to an isolated DNA polynucleotide or nucleic acid molecule, or any fragment, derivative, or complement thereof. It may be double-stranded, single-stranded, or triple-stranded, it may have originated recombinantly or synthetically, and it may represent coding and/or noncoding 5' and/or 3' sequences.

The nucleic acid agent of the present invention, for example, may be a plasmid. Such a plasmid may comprise a nucleic acid sequence encoding cyclin or another cyclin-associated protein, although it is to be understood that other types of nucleic acid agents, such as recombinant viral vectors, may also be used for the purposes of the present invention. In one embodiment of the present invention, the nucleic acid (e.g., plasmid) encodes at least one cyclin-associated protein. Preferably, the nucleic acid encodes cyclin A2 protein.

The term "plasmid", as used herein, refers generally to circular double-stranded DNA, which is not bound to a chromosome. The DNA, for example, may be a chromosomal or episomal-derived plasmid. The plasmid of the present invention may optionally contain a terminator of transcription; a promoter; and/or a discrete series of restriction-endonuclease recognition sites, located between the promoter and the terminator. In the plasmid, a polynucleotide insert of interest (e.g., one encoding a cyclin-associated protein) should be operatively linked to an appropriate promoter. The promoter may be its native promoter or a host-derived promoter. The promoter may also be a tissue-specific promoter, such as a cardiomyocyte-specific promoter or other heart-tissue-specific promoter. The promoter may further be a regulatable promoter, which may be turned off when the expression of the gene is no longer desired. Examples of promoters for use in the present invention include the actin promoter and viral promoters. Other suitable promoters will be known to the skilled artisan.

In another embodiment of the present invention, the nucleic acid (e.g., plasmid) encodes or comprises at least one gene-silencing cassette, wherein the cassette is capable of silencing the expression of genes that negatively affect the cyclin signal-transduction pathway/system. It is well understood in the art that a gene may be silenced at a number of stages, including, without limitation, pre-transcription silencing, transcription silencing, translation silencing, post-transcription silencing, and post-translation silencing. In one embodiment of the present invention, the gene-silencing cassette encodes or comprises a post-transcription gene-silencing composition, such as antisense RNA or RNAi. Both antisense RNA and RNAi may be produced in vitro, in vivo, ex vivo, or in situ.

For example, the cyclin-associated agent of the present invention may be an antisense RNA. Antisense RNA is an RNA molecule with a sequence complementary to a specific RNA transcript, or mRNA, whose binding prevents further processing of the transcript or translation of the mRNA. Antisense molecules may be generated, synthetically or recombinantly, with a nucleic-acid vector expressing an antisense gene-silencing cassette. Such antisense molecules may be single-stranded RNAs or DNAs, with lengths as short as 15-20 bases or as long as a sequence complementary to the entire mRNA. RNA molecules are sensitive to nucleases. To afford protection against nuclease digestion, an antisense deoxyoligonucleotide may be synthesized as a phosphorothioate, in which one of the nonbridging oxygens surrounding the phosphate group of the deoxynucleotide is replaced with a sulfur atom (Stein et al., Oligodeoxynucleotides as inhibitors of gene expression: a review. *Cancer Res.*, 48:2659-68, 1998).

Antisense molecules designed to bind to the entire mRNA may be made by inserting cDNA into an expression plasmid in the opposite or antisense orientation. Antisense molecules may also function by preventing translation initiation factors from binding near the 5' cap site of the mRNA, or by interfering with interaction of the mRNA and ribosomes (e.g., U.S. Pat. No. 6,448,080, Antisense modulation of WRN expression; U.S. Patent Application No. 2003/0018993, Methods of gene silencing using inverted repeat sequences; U.S. Patent Application No., 2003/0017549, Methods and compositions for expressing polynucleotides specifically in smooth muscle cells in vivo; Tavian et al., Stable expression of antisense urokinase mRNA inhibits the proliferation and invasion of human hepatocellular carcinoma cells. *Cancer Gene Ther.*, 10:112-20, 2003; Maxwell and Rivera, Proline oxidase induces apoptosis in tumor cells and its expression is absent or reduced in renal carcinoma. *J. Biol. Chem.*, 278: 9784-89, 2003; Ghosh et al., Role of superoxide dismutase in survival of Leishmania within the macrophage. *Biochem. J.*, 369:447-52, 2003; and Zhang et al., An anti-sense construct of full-length ATM cDNA imposes a radiosensitive phenotype on normal cells. *Oncogene*, 17:811-8, 1998).

Oligonucleotides antisense to a member of the cyclin signal-transduction pathway/system may be designed based on the nucleotide sequence of the member of interest. For example, a partial sequence of the nucleotide sequence of interest (generally, 15-20 base pairs), or a variation sequence thereof, may be selected for the design of an antisense oligonucleotide. This portion of the nucleotide sequence may be within the 5' domain. A nucleotide sequence complementary to the selected partial sequence of the gene of interest, or the selected variation sequence, then may be chemically synthesized using one of a variety of techniques known to those skilled in the art, including, without limitation, automated synthesis of oligonucleotides having sequences which correspond to a partial sequence of the nucleotide sequence of interest, or a variation sequence thereof, using commercially-available oligonucleotide synthesizers, such as the Applied Biosystems Model 392 DNA/RNA synthesizer.

Once the desired antisense oligonucleotide has been prepared, its ability to augment cyclin then may be assayed. For example, the antisense oligonucleotide may be contacted with heart tissue cells or SP progenitor cells, and the levels of cyclin expression or activity in the cells may be determined using standard techniques, such as Western-blot analysis and immunostaining. Alternatively, the antisense oligonucleotide may be delivered to heart tissue cells or SP progenitor cells using a liposome vehicle, then the levels of cyclin expression or activity in the cells may be determined using standard techniques, such as Western-blot analysis and immunostaining. Where the level of cyclin expression in the cells is increased in the presence of the designed antisense oligonucleotide, it may be concluded that the oligonucleotide could be an appropriate cyclin-associated agent for use in augmenting cyclin in heart tissue cells or SP progenitor cells.

It is within the confines of the present invention that oligonucleotides antisense to a member of the cyclin signal-transduction pathway/system may be linked to another agent, such as a drug or a ribozyme, in order to increase the effectiveness of treatments using cyclin-associated agents and/or to increase the efficacy of targeting. Moreover, antisense oligonucleotides may be prepared using modified bases (e.g., a phosphorothioate), as discussed above, to make the oligonucleotides more stable and better able to withstand degradation.

The cyclin-associated agent of the present invention also may be an interfering RNA, or RNAi, including cyclin small interfering RNA (siRNA). As used herein, "RNAi" refers to a double-stranded RNA (dsRNA) duplex of any length, with or without single-strand overhangs, wherein at least one strand, putatively the antisense strand, is homologous to the target mRNA to be degraded. As further used herein, a "double-stranded RNA" molecule includes any RNA molecule, fragment, or segment containing two strands forming an RNA duplex, notwithstanding the presence of single-stranded overhangs of unpaired nucleotides. Additionally, as used herein, a double-stranded RNA molecule includes single-stranded RNA molecules forming functional stem-loop structures, such that they thereby form the structural equivalent of an RNA duplex with single-strand overhangs. The double-stranded RNA molecule of the present invention may be very large, comprising thousands of nucleotides; preferably, however, it is small, in the range of 21-25 nucleotides. In a preferred embodiment, the RNAi of the present invention comprises a double-stranded RNA duplex of at least 19 nucleotides.

In one embodiment of the present invention, RNAi is produced in vivo by an expression vector containing a gene-silencing cassette coding for RNAi. See, e.g., U.S. Pat. No. 6,278,039, *C. elegans* deletion mutants; U.S. Patent Application No. 2002/0066664, Arrayed transfection method and uses related thereto; WO 99/32619, Genetic inhibition by double-stranded RNA; WO 01/29058, RNA interference pathway genes as tools for targeted genetic interference; WO 01/68836, Methods and compositions for RNA interference; and WO 01/96584, Materials and methods for the control of nematodes. In another embodiment of the present invention, RNAi is produced in vitro, synthetically or recombinantly, and transferred into the microorganism using standard molecular-biology techniques. Methods of making and transferring RNAi are well known in the art: see, e.g., Ashrafi et al., Genome-wide RNAi analysis of *Caenorhabditis elegans* fat regulatory genes. *Nature*, 421:268-72, 2003; Cottrell et al., Silence of the strands: RNA interference in eukaryotic pathogens. *Trends Microbiol.*, 11:37-43, 2003; Nikolaev et al., Parc. A Cytoplasmic Anchor for p53. Cell, 112:29-40, 2003; Wilda et al., Killing of leukemic cells with a BCR/ABL fusion gene RNA interference (RNAi). *Oncogene*, 21:5716-24, 2002; Escobar et al., RNAi-mediated oncogene silencing confers resistance to crown gall tumorigenesis. *Proc. Natl. Acad. Sci. USA*, 98:13437-42, 2001; and Billy et al., Specific interference with gene expression induced by long, double-stranded RNA in mouse embryonal teratocarcinoma cell lines. *Proc. Natl. Acad. Sci. USA*, 98:14428-33, 2001.

In a further embodiment of the present invention, the plasmid is an expression plasmid. The expression plasmid may contain sites for transcription initiation, termination, and, optionally, in the transcribed region, a ribosome-binding site for translation. The coding portions of the mature transcripts expressed by the plasmid may include a translation-initiating codon at the beginning, and a termination codon appropriately positioned at the end of the polypeptide to be translated.

By way of example, the cyclin-associated gene to be expressed from the expression plasmid may be under the specific regulatory control of certain types of promoters. In one embodiment, these promoters are constitutive promoters. Genes under the control of these constitutive promoters will be expressed continually. In another embodiment, the promoters are inducible promoters. Genes under the control of these inducible promoters will be expressed only upon the presence of an inducer molecule or the absence of an inhibitor molecule, thereby providing a method to turn off expression of the gene when it is not desired. In yet another embodiment, the promoters are cell-type-specific promoters or tissue-specific (e.g., heart-tissue-specific) promoters. Genes under the control of cell-type-specific promoters will be expressed only in certain cell types, preferably only in cardiomyocytes.

In another embodiment of the present invention, the cyclin-associated agent is a modulator (e.g., inhibitor, activator, antagonist, or agonist) of cyclin expression/activity, including a modulator of a member of the cyclin signal-transduction pathway/system. The modulator of the present invention may be a protein, polypeptide, peptide, nucleic acid (including DNA or RNA), antibody, Fab fragment, $F(ab')_2$ fragment, molecule, compound, antibiotic, or drug, including an agent reactive with cyclin, and an agent that induces or upregulates cyclin expression or activity.

Modulators of cyclin or a member of the cyclin signal-transduction pathway/system may be identified using a simple screening assay. For example, to screen for candidate modulators of cyclin, heart tissue cells or SP progenitor cells may be plated onto microtiter plates, then contacted with a library of drugs. Any resulting increase in, or upregulation of, cyclin expression then may be detected using a luminescence reporter, nucleic acid hybridization, and/or immunological techniques known in the art, including an ELISA. Additional modulators of cyclin expression may be identified using screening procedures well known in the art or disclosed herein. It is within the confines of the present invention that the modulator of cyclin expression may be linked to another agent, or administered in combination with another agent, such as a drug or a ribozyme, in order to increase the effectiveness of treatments using cyclin-associated agents and/or increase the efficacy of targeting. Additional cyclin-associated agents may be identified using screening procedures well known in the art, and methods described herein.

It is also within the confines of the present invention to augment cyclin in heart tissue cells or side-population (SP) progenitor cells by contacting the cells with stem cells (e.g., hematopoietic stem cells or heart-derived stem cells) containing augmented cyclin. The stem cells may be obtained from any animal, but are preferably obtained from a mammal (e.g., human, domestic animal, or commercial animal).

The efficacy of this technique could be assessed, for example, using a cyclin A2 mouse model, in which all cells of the transgenic animal contain an α-MHC-cyclin A2 transgene (as described below). By way of example, female wild-type mice may be subjected to myocardial infarction via ligation of the left-anterior descending (LAD) artery. These mice then may be lethally irradiated. Hematopoietic stem cells (HSCs) purified from male cyclin A2 transgenic mice then may be injected, via the tail vein, into the infarcted, female wild-type mice. For a control group, HSCs from wild-type male mice may be injected into a separate group of infarcted, female wild-type mice. Fluorescence in situ hybridization techniques may be utilized to identify the Y-chromosome, for the purpose of confirming that transdifferentiated stem cells are donor-derived (Gussoni et al., Dystrophin expression in the mdx mouse restored by stem cell transplantation. *Nature*, 401:390-94, 1999).

It is expected that HSCs derived from α-MHC-cyclin A2 transgenic mice will transfer cyclin A2 upon fusing with native heart tissue cells (e.g., cardiomyocytes) or SP progenitor cells, and thereby contribute to cardiac regeneration. Thus, cyclin may be augmented in heart tissue cells or side-population (SP) progenitor cells by contacting the cells with stem cells in which cyclin is already augmented. Furthermore, it is expected that stem cells which transdifferentiate into heart tissue cells (e.g., cardiomyocytes) will retain proliferative potential, and augmented cyclin, instead of transdifferentiating into post-mitotic heart tissue cells. Thus, cyclin also may be augmented in heart tissue cells by augmenting cyclin in stem cells, and allowing such stem cells to differentiate into heart tissue cells that retain proliferative potential and that retain augmented cyclin.

As discussed above, the present invention contemplates the use of proteins and protein analogues generated by synthesis of polypeptides in vitro, e.g., by chemical means or in vitro translation of mRNA. For example, cyclin may be synthesized by methods commonly known to one skilled in the art (*Modern Techniques of Peptide and Amino Acid Analysis* (New York: John Wiley & Sons, 1981; Bodansky, *M., Principles of Peptide Synthesis* (New York: Springer-Verlag New York, Inc., 1984)). Examples of methods that may be employed in the synthesis of the amino acid sequences, and analogues of these sequences, include, but are not limited to, solid-phase peptide synthesis, solution-method peptide synthesis, and synthesis using any of the commercially-available peptide synthesizers. The amino acid sequences of the present invention may contain coupling agents and protecting groups, which are used in the synthesis of protein sequences, and which are well known to one of skill in the art.

In accordance with the method of the present invention, cyclin in heart tissue cells or side-population (SP) progenitor cells may be augmented, and cells may be contacted with a cyclin-associated agent (e.g., by introducing a cyclin-associated agent directly into the cells)—including stem cells containing a cyclin-associated agent—either in vitro, or in vivo in a subject. Where cells are contacted with a cyclin-associated agent in vitro, the agent may be added directly to the cell-culture medium. Alternatively, a cyclin-associated agent may be contacted with heart tissue cells or side-population (SP) progenitor cells in vivo in a subject, by introducing the agent into the subject (e.g., by introducing the agent directly into heart tissue or heart tissue cells of the subject) and/or administering the agent to the subject. The subject may be any animal, including amphibians, birds, fish, mammals, and marsupials, but is preferably a mammal (e.g., a human; a domestic animal, such as a cat, dog, monkey, mouse, and rat; or a commercial animal, such as a cow or pig). In a preferred embodiment, the subject is a human.

The cyclin-associated agent of the present invention (including stem cells containing the agent) may be contacted with heart tissue cells or SP progenitor cells, either in vitro, or in vivo (including in situ) in a subject, by known techniques used for the introduction and administration of proteins, nucleic acids, and other drugs. Examples of methods for contacting the cells with (i.e., treating the cells with) a cyclin-associated agent (in protein or nucleic acid form, and including protein or nucleic acid contained within stem cells) include, without limitation, absorption, electroporation, immersion, injection (including microinjection), introduction, liposome delivery, stem cell fusion (including embryonic stem cell fusion), transduction, transfection, transfusion, vectors, and other protein-delivery and nucleic-acid-delivery vehicles and methods.

When the heart tissue cells (including heart-tissue SP progenitor cells) are localized to a particular portion of a subject, it may be desirable to introduce the agent directly to the cells, by injection or by some other means (e.g., by introducing the agent into the blood or another body fluid). Preferably, where heart tissue cells are contacted with a cyclin-associated agent (including stem cells containing the agent) in vivo in a subject, contacting is accomplished via a catheter inserted directly into the subject's heart tissue. A catheter would be useful in achieving targeted delivery of the agent to heart tissue cells. Targeted delivery is especially appropriate for cardiomyocytes, which are joined by intercalated disks. These disks should allow passage of the agent from one cardiomyocyte to adjoining cardiomyocytes, thereby aiding in the distribution of the agent throughout the heart tissue.

Where a cyclin-associated agent is a protein, it may be introduced into heart tissue cells or SP progenitor cells directly, in accordance with conventional techniques and methods disclosed herein. Additionally, a protein agent may be introduced into heart tissue cells or SP progenitor cells indirectly, by introducing into the cells a nucleic acid encoding the agent, in a manner permitting expression of the protein agent. The cyclin-associated agent may be introduced into cells, in vitro or in vivo, using conventional procedures known in the art, including, without limitation, electroporation, DEAE dextran transfection, calcium phosphate transfection, monocationic liposome fusion, polycationic liposome fusion, protoplast fusion, creation of an in vivo electrical field, DNA-coated microprojectile bombardment, injection with recombinant replication-defective viruses, homologous recombination, in vivo gene therapy, ex vivo gene therapy, viral vectors, and naked DNA transfer, or any combination thereof. Recombinant viral vectors suitable for gene therapy include, but are not limited to, vectors derived from the genomes of such viruses as retrovirus, HSV, adenovirus, adeno-associated virus, Semiliki Forest virus, cytomegalovirus, lentivirus, and vaccinia virus.

By way of example, exogenous cyclin may be contacted with heart tissue cells or SP progenitor cells using an adenovirus vector, such as a replication-deficient (E1, E3 deleted) adenovirus vector containing a transgene encoding an exogenous cyclin (e.g. human cyclin A2) and a strong promoter (e.g., the constitutively-active cytomegalovirus (CMV) promoter). To assess the efficacy of this method, the vector may be prepared, and administered to a test animal as previously described (Chatterjee et al., Viral gene transfer of the antiapoptotic factor Bcl-2 protects against chronic postischemic heart failure. *Circulation,* 106 (12 Suppl. 1):I212-I217, 2002). Cardiac function at 2-, 4-, or 6-week intervals then may be assessed utilizing echocardiography, and regional wall motion may be assessed utilizing sonomicrometry (Chatterjee et al., Viral gene transfer of the antiapoptotic factor bcl-2 protects against chronic postischemic heart failure. *Circulation:I*212-I217, 2002). Mitoses may be assayed using double-immunofluorescence staining with anti-phosphohistone-3, to identify mitotic nuclei; cardiomyocyte cytoplasm may be identified with antibody to alpha-sarcomeric actin.

The amount of nucleic acid to be used in the method of the present invention is an amount sufficient to express an amount of protein effective to promote generation of heart tissue. These amounts may be readily determined by the skilled artisan. It is also within the confines of the present invention to use an ex vivo approach, wherein a nucleic acid encoding a protein agent is introduced into suitable heart tissue cells or SP progenitor cells in vitro, using conventional procedures, to achieve expression of the protein agent in the cells. Cells expressing protein agent are then introduced into a subject to generate heart tissue in vivo.

In accordance with the method of the present invention, a cyclin-associated agent, including stem cells containing the agent, may be administered to a human or animal subject by known procedures, including, without limitation, oral administration, parenteral administration, transdermal administration, and by way of a catheter. For example, the agent may be administered parenterally, by intracranial, intraspinal, intrathecal, or subcutaneous injection. The agent of the present invention also may be administered to a subject in accordance with any of the above-described methods for effecting in vivo contact between heart tissue cells or SP progenitor cells and cyclin-associated agents. Preferably, the agent is administered to the subject by way of targeted delivery to heart tissue cells via a catheter inserted into the subject's heart.

For oral administration, a formulation comprising the cyclin-associated agent may be presented as capsules, tablets, powders, granules, or as a suspension. The formulation may have conventional additives, such as lactose, mannitol, cornstarch, or potato starch. The formulation also may be presented with binders, such as crystalline cellulose, cellulose derivatives, acacia, cornstarch, or gelatins. Additionally, the formulation may be presented with disintegrators, such as cornstarch, potato starch, or sodium carboxymethylcellulose. The formulation also may be presented with dibasic calcium phosphate anhydrous or sodium starch glycolate. Finally, the formulation may be presented with lubricants, such as talc or magnesium stearate.

For parenteral administration (i.e., administration by injection through a route other than the alimentary canal) or administration through a catheter, a cyclin-associated agent may be combined with a sterile aqueous solution that is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulation may be presented in unit or multi-dose containers, such as sealed ampoules or vials. The formulation may be delivered by any mode of injection, including, without limitation, epifascial, intracapsular, intracranial, intracutaneous, intrathecal, intramuscular, intraorbital, intraperitoneal, intraspinal, intrasternal, intravascular, intravenous, parenchymatous, subcutaneous, or sublingual, or by way of a catheter.

For transdermal administration, an agent may be combined with skin penetration enhancers, such as propylene glycol, polyethylene glycol, isopropanol, ethanol, oleic acid, N-methylpyrrolidone, and the like, which increase the permeability of the skin to the agent, and permit the agent to penetrate through the skin and into the bloodstream. The agent/enhancer composition also may be further combined with a polymeric substance, such as ethylcellulose, hydroxypropyl cellulose, ethylene/vinylacetate, polyvinyl pyrrolidone, and the like, to provide the composition in gel form, which may be dissolved in solvent, such as methylene chloride, evaporated to the desired viscosity, and then applied to backing material to provide a patch.

It is believed that, by promoting generation of heart tissue, the method described herein will be particularly useful in repopulating degenerated (damaged or injured) heart tissue in a subject, through either in vitro generation of heart tissue and subsequent transplant thereof into a subject (e.g., a subject in need thereof), or in vivo/in situ generation/regeneration of heart tissue. Accordingly, the present invention provides a method for treating heart tissue degeneration in a subject (e.g., a subject in need of treatment), by promoting generation of heart tissue in accordance with the methods described herein, and transplanting the heart tissue into the subject, thereby treating the heart tissue degeneration. As used herein, the term "transplanting the heart tissue into the subject" includes grafting the heart tissue onto the subject's heart, particularly where the subject's heart tissue is degenerated. The heart tissue transplanted into the subject would, of necessity, include some or all of the heart tissue cells in which cyclin was augmented, as well as some or all of the new heart tissue generated by the present method—which would also comprise heart tissue cells, or side-population (SP) progenitor cells, or stem cells in which cyclin is augmented.

As used herein, "heart tissue degeneration" means a condition of deterioration of heart tissue, wherein the heart tissue changes to a lower or less functionally-active form. As described above, heart tissue damage or degeneration may be caused by, or associated with, a variety of disorders, conditions, and factors, including, without limitation, chronic heart damage, chronic heart failure, injury and trauma, cardiotoxins, radiation, oxidative free radicals, decreased blood flow, and myocardial infarction. Preferably, the heart tissue degeneration of the present invention was caused by myocardial infarction or heart failure.

By way of example, the method of the present invention may comprise the following steps: (a) obtaining or generating a population of heart tissue cells, side-population (SP) progenitor cells, or stem cells; (b) augmenting cyclin in the cells; and (c) transplanting into the subject the cells containing augmented cyclin, and their progeny, if any, in an amount effective to treat the heart tissue degeneration. As discussed above, heart tissue cells containing augmented cyclin would include the original heart tissue cells in which cyclin was augmented and any progeny which contributed to the formation of the newly-generated heart tissue. Thus, heart tissue generation may initially arise in vitro, in the culture of heart tissue cells, SP progenitor cells, or stem cells, but may continue in vivo once transplanted into the subject. In one embodiment of the invention, the subject is a non-human animal. In another embodiment, the subject is a human. Preferably, the subject has heart tissue degeneration. In one embodiment of the invention, the subject is a candidate for, or is recovering from, myocardial infarction. In another embodiment, the subject has, or is a candidate for, chronic heart failure.

The heart tissue generated by the method of the present invention may be transplanted into a subject (e.g., a subject in need of treatment) by standard procedures known in the art, as well as methods described herein. By way of example, heart tissue cells, side-population (SP) progenitor cells, or stem cells may be contacted with a cyclin-associated agent, to promote heart tissue generation. At an appropriate time post-contact, the heart tissue/cells may be prepared for transplantation (e.g., partially triturated), and then transplanted into a subject. To accommodate transplanted tissue, the subject may be suction-lesioned prior to implantation.

In one embodiment of the present invention, the transplanted heart tissue cells, side-population (SP) progenitor cells, or stem cells contain a transgene that has been engineered to express a cyclin-associated agent on an inducible promoter. In this embodiment of the present invention, the agent may be expressed in the presence of a suitable inducer, thereby permitting propagation of the heart tissue cells, SP progenitor cells, or stem cells in vitro. Once the cells are transplanted into the subject, however, the inducing agent would be withdrawn, resulting in decreased expression of the agent, and thereby preventing hyperplasia. Expression of the agent would be sustained in the presence of the inducer, and would be shut down once the supply of inducer was depleted (e.g., upon transplant into a subject).

In the method of the present invention, the heart tissue is transplanted into a subject (e.g., a subject in need of treatment) in an amount effective to treat the heart tissue degeneration. As used herein, the phrase "effective to treat the heart tissue degeneration" means effective to ameliorate or minimize the clinical impairment or symptoms of the heart tissue degeneration. For example, where the heart tissue degeneration results from a myocardial infarction, the clinical impairment or symptoms of the myocardial infarction may be ameliorated or minimized by increasing the number of cardiomyocytes in the subject, increasing heart muscle mass, reducing muscle atrophy, and restoring cardiac function (including ventricular function). The amount of heart tissue effective to treat nervous tissue degeneration in a subject (e.g., a subject in need of treatment) will vary depending upon the particular factors of each case, including the type of heart tissue degeneration, the subject's weight, the severity of the subject's condition, the types of cells in the heart tissue, and the method of transplantation. This amount may be readily determined by the skilled artisan, based upon known procedures, including clinical trials, and methods disclosed herein.

The method of the present invention may also be used either to treat heart tissue degeneration in vivo in a subject, or to prevent heart tissue degeneration in vivo in a subject. As the inventors have demonstrated, augmented cyclin in heart tissue cells or SP progenitor cells has the ability to promote generation (including regeneration) of heart tissue following injury or degeneration, whether the cyclin is augmented prior to the heart tissue degeneration or after. Additionally, the inventors have demonstrated that augmented cyclin in heart tissue cells has a protective effect on the cells, aiding in the prevention of heart tissue degeneration (e.g., degeneration resulting from myocardial injury) that arises after cyclin has been augmented in the cells. In particular, it appears that augmented cyclin in heart tissue cells conditions them to respond to degeneration, such as damage or injury, essentially by repairing themselves.

Accordingly, the present invention provides a method for preventing future heart tissue degeneration, comprising augmenting cyclin in stem cells, or side-population (SP) progenitor cells, or in cells of heart tissue, either in vitro or in vivo in a subject. Furthermore, the present invention provides a method for treating or preventing heart tissue degeneration in a subject (e.g., a subject in need), by promoting generation of heart tissue, in accordance with the methods described herein, through in vivo augmentation of cyclin in heart tissue cells (e.g., cardiomyocytes, heart-tissue SP progenitor cells, etc.) of the subject. By way of example, the method of the present invention may comprise administering to the subject an amount of a cyclin-associated agent (including stem cells containing a cyclin-associated agent) effective to treat or prevent the heart tissue degeneration. This amount may be determined by a skilled artisan.

In one embodiment of the invention, the subject has heart tissue degeneration. Preferably, the subject is recovering from a myocardial infarction, or has chronic heart failure. In another embodiment of the invention, the subject is believed to be a candidate for, or at risk of developing, heart tissue degeneration in the future (e.g., based on certain health indicators, including those based on family history and/or personal history, such as smoking, alcohol consumption, high fat intake, high cholesterol, etc.). Preferably, the subject is a candidate for a myocardial infarction or chronic heart failure.

In view of the foregoing methods, the present invention also provides use of a cyclin-associated agent in the generation of heart tissue. Additionally, the present invention provides use of a cyclin-associated agent in the treatment or prevention of heart tissue degeneration.

The present invention also provides a therapeutic composition comprising a cyclin-associated agent and, optionally, a pharmaceutically-acceptable carrier. As described above, the cyclin-associated agent may include a cyclin protein or nucleic acid, a cyclin-associated protein, a cyclin-associated nucleic acid, a member of the cyclin signal-transduction pathway (including upstream and downstream effectors and activators, in protein or nucleic acid form), and a modulator (e.g., inhibitor, activator, antagonist, or agonist) of a member of the cyclin signal-transduction pathway/system (i.e., a modulator which affects the expression and/or activity of cyclin or a member of the cyclin signal-transduction pathway). In a preferred embodiment, the cyclin-associated agent is a nucleic acid encoding cyclin A2.

In accordance with the therapeutic composition of the present invention, the pharmaceutically-acceptable carrier must be "acceptable" in the sense of being compatible with the other ingredients of the composition, and not deleterious to the recipient thereof. The pharmaceutically-acceptable carrier employed herein is selected from various organic or inorganic materials that are used as materials for pharmaceutical formulations, and which may be incorporated as analgesic agents, buffers, binders, disintegrants, diluents, emulsifiers, excipients, extenders, glidants, solubilizers, stabilizers, suspending agents, tonicity agents, vehicles, and viscosity-increasing agents. If necessary, pharmaceutical additives, such as antioxidants, aromatics, colorants, flavor-improving agents, preservatives, and sweeteners, may also be added. Examples of acceptable pharmaceutical carriers include, without limitation, carboxymethyl cellulose, crystalline cellulose, glycerin, gum arabic, lactose, magnesium stearate, methyl cellulose, powders, saline, sodium alginate, sucrose, starch, talc, and water, among others.

Formulations of the therapeutic composition of the present invention may be prepared by methods well-known in the pharmaceutical arts. For example, a cyclin-associated agent may be brought into association with a carrier or diluent, as a suspension or solution. Optionally, one or more accessory ingredients (e.g., buffers, flavoring agents, surface active agents, and the like) also may be added. The choice of carrier will depend upon the route of administration. The therapeutic composition would be useful for administering the cyclin-associated agent of the present invention to a subject to treat or prevent heart tissue degeneration, as discussed above. The cyclin-associated agent is provided in an amount that is effective to treat or prevent the heart tissue degeneration in a subject to whom the therapeutic composition is administered. This amount may be readily determined by the skilled artisan.

In one embodiment of the present invention, the cyclin-associated agent is a protein that is expressed in a target heart tissue cell or stem cell using an expression construct. Expression of the protein may be controlled by methods known in the art, including the use of attenuators, downregulators, inhibitors, and other molecules known to inhibit protein expression. By way of example, where the therapeutic composition of the present invention is administered to a subject, such that the composition expresses a cyclin-associated protein in the subject, this expression may be shut off in vivo by subsequently administering to the subject an attenuator, downregulator, inhibitor, or other molecule that will inhibit expression of the exogenous molecule. Control of expression of the cyclin-associated protein is also advantageous, in that it allows one to turn off the expression of the protein when desired, thereby minimizing any harmful side-effects in a subject to whom the composition is administered. Continuous expression of such a protein, beyond an appropriate time limit, may harm the subject. For example, a significant interference with a cyclin signal-transduction pathway may cause neoplasia or apoptosis.

The therapeutic composition of the present invention may further comprise a vehicle for assisting in the delivery of the composition to target heart tissue cells, SP progenitor cells, or stem cells. A variety of biological delivery systems (e.g., antibodies, bacteria, liposomes, and viral vectors) currently exist for delivering drugs, genes, immunostimulators, prodrug converting enzymes, radiochemicals, and other therapeutic agents to the vicinity of target cells: see, e.g., Ng et al., An anti-transferrin receptor-avidin fusion protein exhibits both strong proapoptotic activity and the ability to deliver various molecules into cancer cells. *Proc. Natl. Acad. Sci. USA,* 99:10706-11, 2002; Mastrobattista et al., Functional characterization of an endosome-disruptive peptide and its application in cytosolic delivery of immunoliposome-entrapped proteins. *J. Biol. Chem.,* 277:27135-43, 2002; Fefer, "Special delivery" to cancer cells. *Blood,* 99:1503-04, 2002; Kwong et al., The suppression of colon cancer cell growth in nude mice by targeting β-catenin/TCF pathway. *Oncogene,* 21:8340-46, 2002; Huser et al., Incorporation of decay-accelerating factor into the baculovirus envelope generates complement-resistant gene transfer vectors. *Nat. Biotechnol.,* 19:451-55, 2001; Lu et al., Polymerizable Fab' antibody fragments for targeting of anticancer drugs. *Nat. Biotechnol.,* 17:1101-04, 1999; and Chu et al., Toward highly efficient cell-type-specific gene transfer with retroviral vectors displaying single-chain antibodies. *J. Virol.,* 71:720-25, 1997. For example, U.S. Pat. No. 6,491,905 provides a prokaryotic cell stably carrying a vector that includes a DNA sequence encoding a purine nucleotide phosphorylase or hydrolase, and the use of such a cell, together with a purine pro-drug, to treat tumors.

In one embodiment of the present invention, the vehicle is a liposome. Liposomal vesicles may be prepared by various methods known in the art, and liposome compositions may be prepared using any one of a variety of conventional techniques for liposome preparation known to those skilled in the art. Examples of such methods and techniques include, without limitation, chelate dialysis, extrusion (with or without freeze-thaw), French press, homogenization, microemulsification, reverse phase evaporation, simple freeze-thaw, solvent dialysis, solvent infusion, solvent vaporization, sonication, and spontaneous formation. Preparation of the liposomes may be carried out in a solution, such as an aqueous saline solution, aqueous phosphate buffer solution, or sterile water. Liposome compositions also may be prepared by various processes involving shaking or vortexing.

The therapeutic composition of the present invention may be incorporated into the layers of a liposome, or enclosed within the interior of the liposome. The liposome containing the composition then may be fused with a target heart tissue cell, SP progenitor cell, or stem cell, in accordance with known methods of fusion of liposomes to cell membranes, such that the composition protein is delivered into the membrane of the cell or into the interior of the cell, as the case may be.

The present invention also provides a kit for use in delivering a cyclin-associated agent to heart tissue cells, SP progenitor cells, or stem cells, particularly cells in a subject. The kit comprises a therapeutic composition and a catheter. As described above, the therapeutic composition may comprise a cyclin-associated agent; optionally, a pharmaceutically-acceptable carrier; and, optionally, a liposome, viral vector, or other vehicle.

The present invention further provides a cell (e.g., a heart tissue cell, a side-population (SP) progenitor cell, a stem cell, etc.) in which the expression/level of at least one cyclin, and/or at least one function, activity, or effect of at least one cyclin, have been augmented. Preferably, the cell is a heart tissue cell (e.g., a cardiomyocyte, a heart-tissue SP progenitor cell, etc.) or a side-population (SP) progenitor cell found in non-heart tissue. The cell may be obtained from, or located in, any animal. In a preferred embodiment, the cell is a human cell. In another preferred embodiment, the cell is obtained from, or located in, a transgenic animal that overexpresses cyclin A2 in its heart tissue, as described below. Additionally, in one embodiment of the present invention, the cyclin is cyclin A2. In another embodiment, the cell overexpresses at least one cyclin, particularly cyclin A2. In a further embodiment of the present invention, the heart tissue cell, SP progenitor cell, or stem cell comprises the therapeutic composition described above.

The heart tissue cell of the present invention may be any cell found in heart tissue, as described above. In one embodiment of the present invention, the heart tissue cell is a cardiomyocyte. The cardiomyocyte may be of adult origin; thus, initially, it would contain no, or an insignificant amount of, cyclin, but would be manipulated to contain a substantial amount of cyclin, or substantially more cyclin that it contained prior to manipulation. The cardiomyocyte may also be of pre-adult or prenatal origin; thus, initially, it would contain a base level of cyclin, but would be manipulated to contain augmented functions, activities, effects, expression, and/or levels of cyclin. Similarly, the SP progenitor cell or stem cell of the present invention may initially contain a base level of cyclin. However, it would be manipulated to contain augmented functions, activities, effects, expression, and/or levels of cyclin. In one embodiment of the present invention, the functions, activities, effects, expression, and/or levels of cyclin in the cell are augmented by contacting the cell with a cyclin-associated agent. In a preferred embodiment of the invention, the cyclin is cyclin A2, and the cells are contacted with a cyclin-A2-associated agent. The agent may be delivered to the heart tissue cell, SP progenitor cell, or stem cell in vitro, in vivo, ex vivo, or in situ, in accordance with methods described above. In one preferred embodiment, the agent is delivered to a heart tissue cell in situ, through a catheter. The present invention also provides a cell line comprising the cell of the present invention and the progenies thereof.

Cardiotoxicity is a side-effect that can occur after treatment with anticancer and other drugs, and which may have severe clinical implications. The heart tissue cell line of the present invention provides a population of cells that may be useful in an in vitro assay that screens for cardiotoxic effects (i.e., poisonous or deleterious effects upon the heart) of a candidate drug that is potentially useful for the treatment of a pediatric disorder. It is known that the levels of certain cyclins are high in the fetal heart, but diminish (often rapidly) after birth, and ultimately disappear by adulthood (Kim et al., *Korean J. Intern. Med.,* 13(2):77-82, 1998; Kang and Koh, *J. Mol. Cell Cardiol.,* 33(10):1769-71, 1997; Yoshizumi et al., *J. Clin. Invest.,* 95(5):2275-80, 1995). The inventors, themselves, have demonstrated that the levels of cyclin A2 are high in the fetal heart, but diminish rapidly after birth, in the perinatal stage. Thus, heart tissue cells having augmented cyclin, particularly cyclin A2, provide a convenient model of prenatal heart cells, and provide a useful assay for identifying drugs that may be cardiotoxic to newborns and children of early age.

The heart tissue cell line of the present invention also may be useful in an in vitro assay that screens candidate agents for synergy with cyclin in the treatment of heart tissue degeneration. In such a system, the tissue-generating effects of augmented cyclin, particularly cyclin A2, would be enhanced or improved in the presence of such a synergistic agent.

Accordingly, the present invention further provides an in vitro system for use in screening for at least one cardiotoxic effect in a candidate drug that is potentially useful for the treatment of a pediatric disorder. This in vitro system comprises a population of heart tissue cells in which a cyclin (preferably, cyclin A2) is augmented. In one embodiment of the invention, the heart tissue cells are obtained from the above-described heart tissue cell line. Additionally, the present invention provides an in vitro system for use in screening a candidate agent for synergy with cyclin in the treatment of heart tissue degeneration. This in vitro system comprises a population of heart tissue cells in which a cyclin preferably, cyclin A2) is augmented. In one embodiment of this invention, the heart tissue cells are obtained from the above-described cell line.

Furthermore, the stem cell line of the present invention may be useful in an i71 vitro assay that screens candidate therapeutics for toxic effects on stem cells, wherein the toxic effects are diminished in the presence of augmented cyclin. Accordingly, the present invention further provides an in vitro system for use in screening for a candidate drug that has at least one toxic effect on stem cells, wherein the toxic effect is prevented or attenuated in the presence of augmented cyclin. This in vitro system comprises a population of stem cells in which a cyclin (preferably, cyclin A2) is augmented. In one embodiment of the invention, the stem cells are obtained from the above-described stem cell line.

The in vitro assays and cell lines of the present invention may be used in various screenings, as described above. Thus, the present invention also provides an in vitro method for screening for at least one cardiotoxic effect in a candidate drug that is potentially useful for the treatment of a pediatric disorder, comprising the steps of: (a) contacting heart tissue cells in which a cyclin (preferably, cyclin A2) is augmented (e.g., cells obtained from the above-described heart tissue cell line) with a candidate drug that is potentially useful for the treatment of a pediatric disorder; and (b) assaying the heart tissue cells for one or more cardiotoxic effects, if any. Examples of a cardiotoxic effect may include, without limitation, heart tissue degeneration, leakage of lactate dehydrogenase, changes in cell morphology, cell membrane lysis, cellular viability, alterations in spontaneous beating activity (Mbugua et al., In vitro Cell Dev. Biol., 24(8):743-52, 1988), depolarization of cell membranes, diminished contractile function of heart tissue cells, a decrease in the number of heart tissue cells, and downregulation of cyclin. Cardiotoxic effects may be measured or detected by known techniques, including Western blotting for heart-specific proteins, electron microscopy in conjunction with morphometry, simple assays to measure rate of cell proliferation, including those described above, and any of the methods, molecular procedures, and assays disclosed herein. The present invention also provides a drug screened or identified by this method.

Additionally, the present invention provides an in vitro method for screening a candidate agent for synergy with cyclin in the treatment or prevention of heart tissue degeneration, comprising the steps of: (a) contacting heart tissue cells in which a cyclin (preferably, cyclin A2) is augmented (e.g., cells obtained from the above-described heart tissue cell line) with a candidate agent; and (b) assessing the ability of the candidate agent to enhance heart tissue generation (e.g., cyclin-mediated heart tissue generation). Where the candidate agent is shown to enhance heart tissue generation, it may have synergy with cyclin in the treatment or prevention of heart tissue degeneration. Enhanced heart tissue generation may be detected, for example, by detecting increased proliferation of heart tissue cells or by detecting an increased rate of division of heart tissue cells. The present invention also provides an agent identified by this method. The present invention further provides a method for treating or preventing heart tissue degeneration in a subject (e.g., a subject in need), by administering to the subject a cyclin-associated agent in combination with the agent identified by the above-described screening method, in amounts effective to treat or prevent heart tissue degeneration. Such amounts may be readily determined by the skilled artisan.

The present invention also provides an in vivo method for screening a candidate agent for synergy with cyclin in the treatment or prevention of heart tissue degeneration, comprising the steps of: (a) contacting heart tissue cells in which a cyclin (preferably, cyclin A2) is augmented (e.g., cells obtained from the above-described heart tissue cell line) with a candidate agent; (b) transplanting the heart tissue cells and their progeny, if any, into a subject; and (c) assessing the ability of the candidate agent to enhance survival of the cells and progeny thereof after transplantation. The ability of the candidate agent to enhance survival of the heart tissue cells, following transplantation, may be assessed by determining whether cells from the cell line are more easily implanted, or more readily incorporated into heart tissue of the subject, in the presence of the candidate agent. Where implantation and/or incorporation are enhanced in the presence of the candidate agent, it may be concluded that the candidate agent has synergy with cyclin in the treatment or prevention of heart tissue degeneration. The present invention also provides an agent identified by this screening method. The present invention further provides a method for treating or preventing heart tissue degeneration in a subject (e.g., a subject in need), comprising administering to the subject a cyclin-associated agent in combination with the agent identified by the above-described screening method, in amounts effective to treat or prevent heart tissue degeneration. Such amounts may be readily determined by the skilled artisan.

The present invention further provides an in vitro method for screening for a candidate drug that has at least one toxic effect on stem cells, wherein the toxic effect is prevented or attenuated in the presence of augmented cyclin, comprising the steps of: (a) contacting stem cells in which a cyclin (preferably, cyclin A2) is augmented (e.g., cells obtained from the above-described stem cell line) with a candidate drug; (b) contacting control stem cells, that do not have augmented cyclin, with the candidate drug; and (c) assaying the stem cells of step (a) and the control stem cells of step (b) for at least one toxic effect, wherein the presence of a toxic effect in the control stem cells of step (b), but an absent, or attenuated, toxic effect in the stem cells of step (a), is indicative that the candidate drug has at least one toxic effect on stem cells, wherein the toxic effect is prevented or attenuated in the presence of augmented cyclin. Toxic effects on stem cells may include, without limitation, changes in cell morphology, cell membrane lysis, changes in cell viability, and depolarization of cell membranes. Such toxic effects may be measured or detected by known techniques, including Western blotting for stem-cell-specific proteins, electron microscopy in conjunction with morphometry, simple assays to measure rate of cell proliferation, including those described above, and any of the methods, molecular procedures, and assays disclosed herein. The present invention also provides a drug screened or identified by this method.

The present invention is described in the following Examples, which are set forth to aid in the understanding of the invention, and should not be construed to limit in any way the scope of the invention as defined in the claims which follow thereafter.

EXAMPLES

In the following Examples, data are expressed as mean±s.e.m. A Student's t-test was used for data comparison, using a significance level of $P<0.05$.

Example 1

Generation of Transgenic Mice

Mouse cyclin A2 cDNA was subcloned into a vector (clone 26 from Dr. Jeffrey Robins, University of Cincinnati, Cincinnati, Ohio) containing alpha-myosin heavy-chain promoter and the human growth hormone polyadenylation site (Subramaniam et al., *J. Biol. Chem.*, 266:24613-20, 1991). Transgenic mice were then generated according to previous protocols on a B6CBA background (Behringer et al., *Development*, 117:823-33, 1993). Specifically, purified insert DNA was microinjected into C57B16/J zygotes, according to the inventors' previous protocols (Behringer et al., *Development*, 117: 823-33, 1993). In brief, the transgene was injected into the male pronuclei of fertilized eggs, at a concentration of 5 ng/µl. The microinjected embryos were then cultured in vitro, to the two-cell stage, and then re-implanted into pseudopregnant CD-1 female mice. All manipulations were performed according to Institutional Animal Care and Use Guidelines. Pups derived from the microinjected embryos were screened for the presence of the transgene by genomic-DNA-blot hybridization (Behringer et al., *Development*, 117:823-33, 1993), utilizing cyclin A2 cDNA as a probe. Positive animals were then used to establish six lines of transgenic mice, which were maintained on a B6CBA background (Behringer et al., *Development*, 117:823-33, 1993). Phenotypic characterization in this study was carried out using the F1 generation.

Example 2

Assessment of Heart Size/Body Weight Ratios

Following body-weight determination for each mouse, the heart was removed after anesthetizing with avertin. KCl (3.0 M) was injected into the beating heart, to induce diastolic arrest. The heart was gently perfused with 1× PBS, and all fat tissue was removed before heart-weight determination was made. Heart-to-body weight ratios were measured for neonatal (PN7, PN14) and adult (3-18 months) transgenic mice, and normal littermate controls.

Example 3

Assessment of Cell Sizes

Whole ventricular sections from adult (6 months) transgenic and normal littermate controls were fixed in 4% paraformaldehyde and embedded in paraffin. Sequential transverse sections (4 µm) were cut and stained with hematoxylin and eosin. Using digital pictures of these sections, cell-analysis software (UTHSCSA Image Tool) was employed to measure cross-sectional areas of myocytes. Similar fields, at 40× magnification for both transgenic and non-transgenic sections, were utilized. At least 200 cells/heart were measured at 6 months of age, for each of two lines (lines 1 and 58), in both transgenic and normal littermate controls. Only cells with clearly-delineated borders were used in these measurements.

Cell lengths were measured utilizing the same program, after immunostaining for pan-cadherin (Sigma, St. Louis, Mo.), an antibody to a structural protein found in the intercalated discs (Bianchi et al., *Circulation*, 104(12 Suppl. 1):I319-24, 2001), was performed. Similar sections of myocytes, in longitudinal sections, at 40× magnification for both transgenic and non-transgenic hearts, were used. Only those myocytes which could be visualized from end to end were used in this determination. At least 200 cell lengths/heart were measured at 6 months of age, for lines 1 and 58, in both transgenic and normal littermate controls.

Example 4

Assessment of Myocyte Number

The weights of 10 transgenic and 10 non-transgenic mice (aged 6 months, male) were obtained. The ventricles were separated from these hearts using a dissecting microscope, and ventricular weights were obtained. The average ventricular weight/total heart weight ratio was computed for transgenic and non-transgenic hearts. From this determination, the ventricular weight was computed for the hearts used in measurements of myocyte cross-sectional area and length. Ventricular weight was multiplied by the known value for specific gravity of muscle tissue (1.06 gm/ml), to obtain ventricular volume (Mendez and Keys, *Metabolism*, 9:184-88, 1960). The calculated ventricular volume was multiplied by 0.82 to determine the fraction occupied by myocytes (Jackson et al., *Mol. Cell. Biol.*, 7:3709-16, 1990). The average volume of each myocyte was calculated by multiplying myocyte cross-sectional area by length. The number of myocytes per ventricle was computed by dividing the myocyte fraction of ventricular volume by the average myocyte volume.

Example 5

Assessment of Cardiomyocyte DNA Synthesis

Whole ventricular sections from embryonic, post-natal, and adult transgenic and normal littermate controls were fixed and embedded in paraffin, as described above. Stages analyzed included E18, PN2, PN7, PN14, and 6 months. Sequential transverse (4 µm) sections were cut and analyzed by immunohistochemistry, as performed previously in the inventors' laboratory (Behringer et al., *Development*, 117: 823-33, 1993). Immunostaining with antibody (1:100) to proliferating cell nuclear antigen (PCNA) (Pharmingen, San Diego, Calif.) was performed as an indicator of DNA synthesis (Haracska et al., *Mol. Cell. Biol.*, 3:784-91, 2002). Sections were analyzed on a Nikon microscope, under brightfield optics. Similar fields for each transgenic versus normal littermate control were compared at 40× magnification, and the number of nuclei staining positively for PCNA were counted per 16,800 µm².

Example 6

Assessment of Cardiomyocyte Nuclei Per Unit Area

Whole ventricular sections from 6-month-old transgenic and non-transgenic mice, from lines 1 and 58, were prepared, as above. Immunofluorescence staining with antibody to α-sarcomeric actin (1:200), to delineate cardiomyocytes, was performed as above; nuclei were stained with DAPI (Molecular Probes, Eugene, Ore.). Nuclei within cardiomyocytes were counted for each field (16,800 µm$^2$), in similar sections from both transgenic and non-transgenic mice.

Example 7

Assessment of Mitosis

Whole ventricular sections, at various developmental stages, were prepared as above. Immunofluorescence staining with antibody (1:50) to phosphorylated histone-3 (H3P, Upstate Biotechnology, Lake Placid, N.Y.) was performed. Phosphorylated histone-3 is a mitosis-specific marker (Wei et al., *Proc. Natl. Acad. Sci.*, 95:7480-84, 1998). Cardiomyocytes were stained with antibody (1:200) to α-sarcomeric actin (Sigma, St. Louis, Mo.). Anti-rabbit rhodamine (Molecular Probes, Eugene, Oreg.) was used as the secondary antibody for the H3P, and anti-mouse IgG FITC (Sigma, St. Louis, Mo.) was used as the secondary against α-sarcomeric actin. Similar fields of ventricular myocardium, for each transgenic versus normal littermate control, were compared at 40× magnification, and the number of cardiomyocyte nuclei staining positively for H3P was counted per 16,800 µm$^2$. The measurements for at least 10 fields were averaged at each developmental stage analyzed. These were counted directly, as viewed on a Nikon photomicroscope under fluorescent-field optics. Rotational analysis for localization to cardiomyocytes was performed using confocal microscopy, through 10-micron-thick sections.

Example 8

Assessment of Cardiac Function MRI Image Acquisition and Analysis

All imaging experiments were performed on a 9.4 Tesla Bruker WB400 microimaging system, with 30 mm quadrature RF coil (Bruker NMR Inc., Bellerica, Mass.). The mice were anesthetized with isoflurane (1.5% vol. in 2 L/min air flow). The heart rate was ~450 bpm. Quantification of ventricles was based on bright blood 2D image stacks that were acquired using ECG-gated fast gradient echo cine sequence. The acquisition parameters were 250 ms repetition time, 1.8 ms echo time, 30° flip angle, 0.1 mm in-plane resolution, 1 mm slice thickness, and 4 min/slice scan time. Eight cardiac points were sampled over the cardiac cycle. The short axis images were acquired, from which the left ventricle and myocardium were semi-automatically segmented using region-growing algorithm and histogram-based thresholding (Tang et al., *Ann. NY Acad. Sci.*, 904:32-41, 2000).

Discussed below are results obtained by the inventors in connection with the experiments of Examples 1-8:

To demonstrate that cyclin A2 is silenced in the mouse heart, shortly after birth, concomitant with withdrawal from mitosis, the relative levels of cyclin A2 mRNA and protein expression were assayed at selected times during murine cardiac development. Northern-blot analysis revealed that cyclin A2 transcripts of 3.0 kb and 1.7 kb were observed at embryonic day 12 (E12), E18, and PN2, but that expression was absent by 6 weeks of age (FIG. 1A). Immunoblot analysis could not detect cyclin A2 protein in lysates of total protein of mouse hearts at PN2, and at later time points (FIG. 1B). The number of ventricular cardiomyocyte nuclei expressing cyclin A2 protein, as detected by immunohistochemical analysis, was high at E14, with a noticeable decline at E18, a further diminution at PN2, and complete absence by 2 weeks of age (FIG. 1C). This temporal pattern of decreased expression of cyclin A2 mRNA and protein levels are consistent with the previously described silencing of cyclin A2 in the hearts of rats and humans shortly after birth (Yoshizumi et al., *J. Clin. Invest.*, 95:2275-80, 1995), which also coincides with cardiomyocyte cell-cycle withdrawal.

Figure 2:
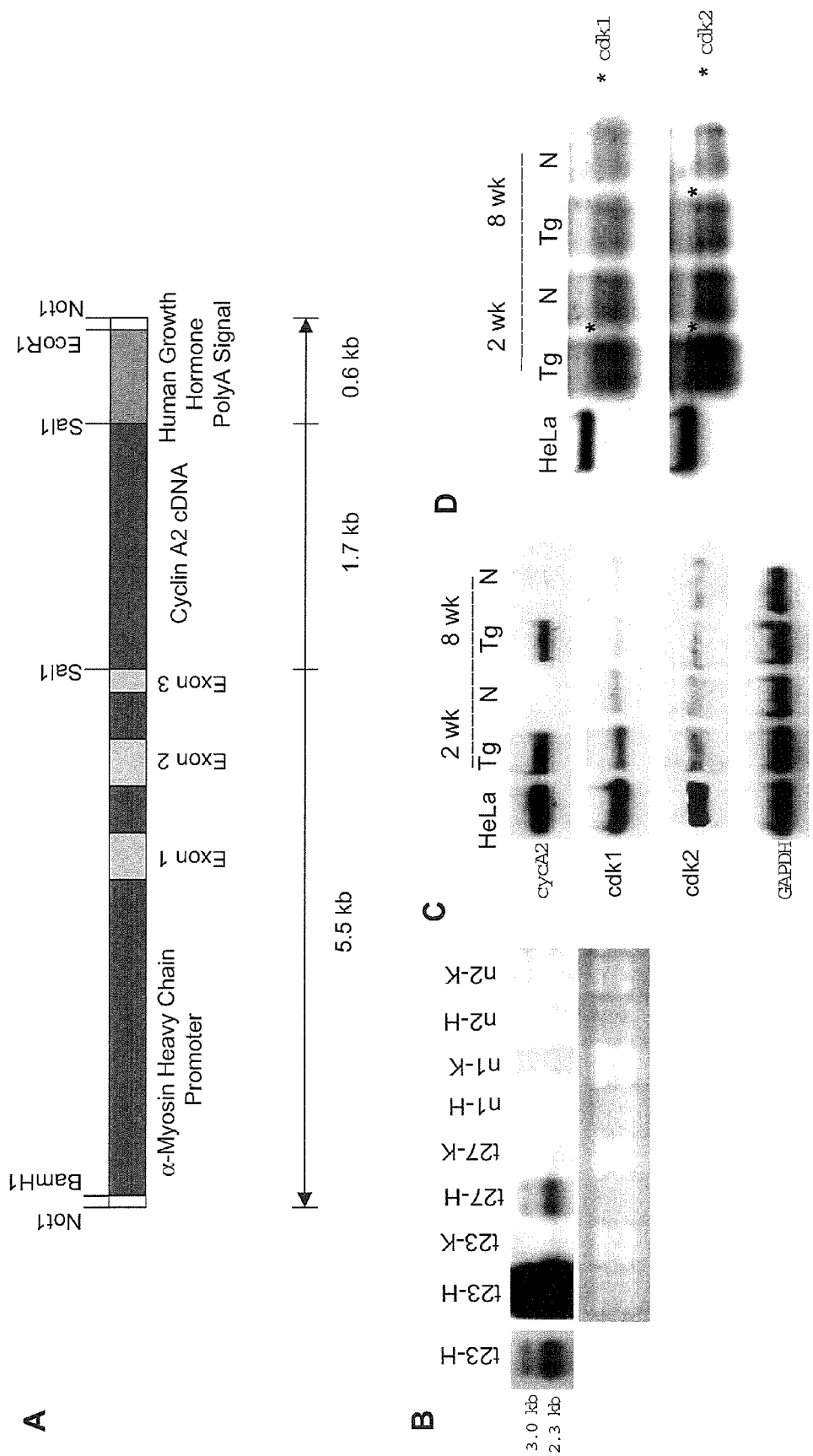
FIG. 2 illustrates that cyclin A2 mRNA and protein expression are restricted to transgenic mouse hearts. (A) Diagram of MHC-CYCA2 transgenic construct. The inventors cloned mouse cDNA, and used a standard construct for the purposes of this invention. (B) Representative Northern-blot analysis of control and transgenic samples. RNA was isolated from transgenic mice (t23 and t27) and normal mice (n1 and n2). The blot was re-exposed for a shorter period of time, to delineate detail in the Ht23 lane. 'H' and 'K' indicate heart and kidney, respectively. The ethidium-bromide-stained ribosomal RNA bands are shown in the bottom panel as a loading control. (C) Immunoblot analysis of cell-cycle protein expression in transgenic (Tg) and normal (N) mice, at 2 weeks and 8 weeks. top panel: α-cyclin A2; second panel from top: cdk1; third panel from top: cdk2; bottom panel: GAPDH sample loading control. HeLa cell lysate was used as a positive control. (D) )Immunoprecipitation analysis of cyclin A2 complexes in transgenic and control hearts, at 2 weeks and 8 weeks. α-cyclin A2 immunoprecipitated complexes (denoted by asterisks) were analyzed by immunoblot analysis with α-cdk1 (top) or α-cdk2 (bottom). The band visualized at 29 kD represents the immunoglobulin light chain. HeLa cell lysate was used as a positive control.

To test the hypothesis that sustained cyclin A2 expression would modulate cardiomyocyte proliferation, transgenic mice that constitutively express cyclin A2 in the cardiomyocyte lineage were generated (Behringer et al., *Development*, 117:823-33, 1993). The α-myosin heavy-chain (MHC) promoter was chosen, as it is expressed throughout embryogenesis, from E7.5, and continues to be expressed through adulthood (Subramaniam et al., *J. Biol. Chem.*, 36:24613-620, 1991) (FIG. 2A). Eight founders were identified after screening 60 pups derived from microinjected embryos; six gave rise to transgenic lineages. There was no obvious morbidity in the MHC-CYCA2 founder mice. Cyclin A2 expression in at least 3 hearts from each line, at 5-7 months of age, was assessed by Northern analysis. A representative blot is shown in FIG. 2B.

Lines 1, 2, 44, and 58 consistently expressed cyclin A2 mRNA, although there was some variation in the levels of expression from animal to animal within the same line. Other adult organs in which cyclin A2 expression has not been detected, such as the kidney (Ravnik and Wolgemuth, *Dev. Biol.*, 173(1):69-78, 1996), failed to show cyclin A2 expression in transgenic mice, consistent with the previously described myocardial specificity of the MHC promoter (Subramaniam et al., *J. Biol. Chem.*, 36:24613-620, 1991). The expected size of the transgenic mRNA transcript was 2.3 kb, as the inventors' transgene had 0.6 kb of human growth hormone poly-adenylation signal attached to the 3' end of the 1.7-kb cyclin A2 cDNA. Interestingly, a 3.0-kb band was also visualized in the lanes containing transgenic heart mRNA. This size was consistent with the larger endogenous transcript, and was absent from the lanes containing non-transgenic heart mRNA. Cyclin A2 protein, assayed by immunoblot analysis, was expressed in transgenic hearts from line 58 at ages 2 weeks and 8 weeks, and was absent from non-transgenic hearts at both time points (FIG. 2C).

To determine if the continued expression of cyclin A2 altered the expression of cdk1 and cdk2, control and transgenic lysates were analyzed by immunoblot analysis at 2 weeks and 8 weeks of age (FIG. 2C). Average 1.6-fold and 1.2-fold increases in the levels of cdk1 protein, at 2 weeks and 8 weeks of age, respectively, were observed in the lysates of total transgenic hearts. These levels were notably different from the low levels of constitutive expression of cdk1 in control littermates. Immunoblot analysis demonstrated low levels of expression of cdk2 in non-transgenic hearts, consistent with previous work reported by other investigators (Oh et al., *Proc. Natl. Acad. Sci.*, 98(18):10308-313, 2001). Interestingly, average 2.5-fold and 2.1-fold increases in the expression of cdk2 in the transgenic heart were observed at 2 weeks and 8 weeks of age, respectively.

To ascertain whether this temporally- and ectopically-expressed cyclin A2 actually complexed with its normal cdk1 or cdk2 partner, immunoprecipitation followed by immunoblot analysis was performed using total heart lysates (FIG. 2D).

Both cyclin A2/cdk1 and cyclin A2/cdk2. complexes were clearly detected at 2 weeks of age in transgenic hearts, but never in non-transgenic hearts. The cyclin A2/cdk2 complex was still detected at 8 weeks in the transgenic hearts, but not in non-transgenic hearts.

Cyclin A2 transgenic mice were fertile, appeared healthy, and were not prone to alteration in morbidity and mortality over one year of observation. No gross morphological abnormalities were noted in the transgenic hearts. However, the heart-weight-to-body-weight ratio (HW/BW) of adult transgenic mice was significantly increased when compared to normal hearts. Cardiac enlargement was actually noted across all lines that expressed cyclin A2 mRNA. However, a closer analysis of this phenotype was undertaken in lines 1 and 58. HW/BW ratios were determined at selected ages from postnatal development through adulthood (specifically, PN7 to 1.5 years of age). There was no significant cardiac enlargement noted at PN7 and PN14. However, the difference between the HW/BW ratios of transgenic versus non-transgenic mice increased with age (FIG. 3A), with statistical significance noted after 6 months of age.

Microarray magnetic resonance imaging (OM) analysis is the most technologically advanced modality currently available for the assessment of cardiac mass and function, and is presently the most accurate and reliable method for noninvasively quantifying left ventricular mass and function in mice (Wiesmami et al., *Am. J. Physiol.*, 278:H653-57, 2000; Slawson et al., *Magn. Reson. Med.*, 39:980-87, 1998). MRI images at end-diastole (at mid-ventricular level) were, therefore, utilized for the assessment of cardiac size in transgenic and normal gender-matched littermates, in line 58, at 8 months of age. The transgenic (n=3) mouse hearts occupied an average of $41.0\pm0.01\%$ of the chest area compared with $30.5\pm0.01\%$ occupied by the normal (n=3) mouse hearts (p=0.0083). Thus, the MRI analysis confirmed that the area of the chest cavity occupied by the heart is larger in the living transgenic mice than in normal littermates.

The inventors went on to examine the possibility that the increase in cardiac size in MHC-CYCA2 mice was due to an increase in connective tissue content. Transverse sections from adult (6 months) transgenic and non-transgenic hearts, from lines 1 and 58, were stained with Masson trichrome, to identify fibrotic tissue. Histologic examination revealed no evidence of increased fibrosis in the cyclin-A2-expressing hearts (data not shown). Therefore, the increased cardiac size of the transgenic hearts was not secondary to changes in the connective tissue content of the heart.

Figure 3:
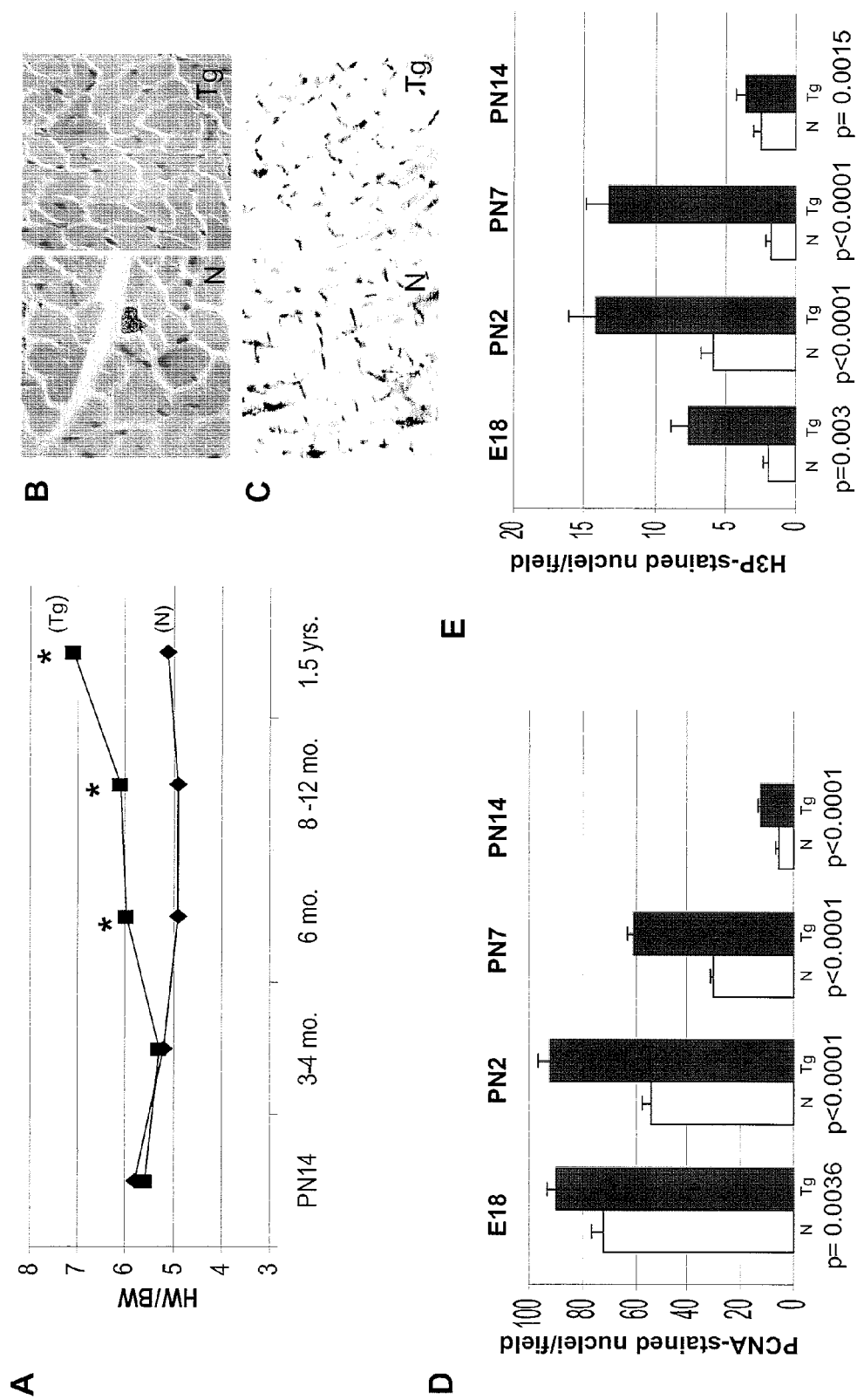
FIG. 3 demonstrates that cyclin A2 transgenic mice exhibit cardiac hyperplasia due to an increase in post-natal mitosis. (A) Enlargement of hearts of cyclin A2 transgenic mice. Heart weight/body weight (HW/BW) ratios (mg/g) of normal and transgenic mice were plotted throughout development, from PN7 through 1.5 years of age. The numbers of transgenic (Tg) and normal (N) mice examined at each age are detailed as follows: PN7 and PN14—16 Tg, 15 N; 3-4 mo—5 Tg, 5 N; 6 mo—10 Tg, 10 N; 8-12 mo—5 Tg, 5 N; 1.5 yr—1 Tg, 1 N. The asterisks indicate ages at which the HW/BW difference between transgenic and normal is statistically significant. (B) Myocyte cross-sectional areas were measured in normal versus transgenic littermates (lines 1 and 58, age 6 mo). Hematoxylin- and eosin-stained sections of normal (N) and transgenic (Tg) ventricular myocardium were analyzed for cross-sectional areas, utilizing Image Tool software. (C) Myocyte lengths, measured in normal versus transgenic littermates (lines 1 and 58, age 6 mo). Pan-cadherin staining of intercalated disks in ventricular myocardium was performed for the measurements of cell lengths in longitudinal sections, utilizing Image Tool software. (D) Proliferating cell nuclear antigen (PCNA) expression in transgenic and control hearts at selected time points through development. The number of positively-stained nuclei per unit area was assessed and averaged over at least ten fields (field size=16,800 $\mu m^2$). With the exception of E18, there was a significant increase in PCNA-stained nuclei per unit area at each developmental stage analyzed in the transgenic mice. (E) Detection of phosphorylated histone H3 in transgenic and normal myocardium. The number of mitotic nuclei (as assessed by phosphorylated histone-3 (H3P) staining) per field was significantly enhanced in transgenic hearts, as compared to normal hearts, at each developmental stage. At least ten fields were analyzed for each value. Green bars indicate transgenic mice, and blue bars indicate the normal controls. P values are indicated below each set. Note the 8-fold increase in mitotic nuclei in transgenic versus normal mice at PN7.

To determine if the continued expression of cyclin A2 resulted in hyperplasia, which would contribute to the enlarged heart phenotype, the inventors calculated the total number of ventricular cardiomyocytes present in the transgenic versus control hearts, at 6 months of age. The first step was to measure cross-sectional areas and myocyte lengths in transgenic and normal mice, at 6 months of age, in lines 1 and 58 (FIGS. 3B, 3C). Myocyte cross-sectional areas were, in fact, slightly reduced, in a statistically-significant manner, in the transgenic hearts, as compared with normal hearts, with an average of $209.7\pm2.32\ \mu m^2$ in the line 1 transgenic mice and $228.2\pm2.29\ \mu m^2$ in the line 1 non-transgenic mice, P<0.0001. In line 58, there was an average cross-sectional area of $193.2\pm2.04\ \mu m^2$ in the transgenic and an average of $231.0\pm2.26\ \mu m^2$ in the non-transgenic, P<0.0001. Myocyte length was found to be shorter in the transgenic hearts, as compared to normal hearts, with an average length of $48.4\pm0.599\ \mu m$ in the line 1 transgenic heart, and $51.9\pm0.583\ \mu m$ in the line 1 non-transgenic, P<0.0001. In line 58, there was an average length of $46.2\pm0.522\ \mu m$ in the transgenic mice, and an average length of $50.2\cong0.567\ \mu m$ in the non-transgenic mice, P<0.0001.

The measurements of cardiomyocyte cross-sectional areas and lengths were utilized to calculate the average myocyte volume in representative hearts from lines 1 and 58 in which the original measurements were made (Table 1). The quotient of the total ventricular volume to the average myocyte volume gave an estimate of the number of myocytes present in each ventricle. There was an average increase of 67.3% in the number of myocytes present in the line 58 transgenic heart, as compared to its normal littermate control, at 6 months of age. In contrast, an average increase of 43.4% was noted in the line 1 transgenic heart, as compared to its normal littermate control, at 6 months of age. The reduction in cardiomyocyte size in the transgenic mouse heart, coupled with the overall increase in cardiac size, demonstrates that constitutive expression of cyclin A2 elicits cardiomyocyte hyperplasia.

TABLE 1

Ventricular myocyte number in transgenic (Tg) versus normal (N) hearts.

| | | Heart Weight (g) | Ventricular Weight (g) | Ventricular Volume (ml) | Myocyte Fraction of Ventricular Volume | Myocyte Volume (ml) | Number of Myocytes | Average Percent Increase |
|---|---|---|---|---|---|---|---|---|
| Line 1 | N | 0.113 | 0.098 | 0.092 | 0.075 | $1.18 \pm 0.025 \times 10^{-8}$ | $6.36 \pm 0.136 \times 10^6$ | 43.4% |
|  | Tg | 0.143 | 0.120 | 0.113 | 0.093 | $1.02 \pm 0.022 \times 10^{-8}$ | $9.12 \pm 0.195 \times 10^6$ |  |
| Line 58 | N | 0.131 | 0.113 | 0.107 | 0.088 | $1.16 \pm 0.025 \times 10^{-8}$ | $7.59 \pm 0.165 \times 10^6$ | 67.3% |
|  | Tg | 0.174 | 0.146 | 0.138 | 0.113 | $0.893 \pm 0.019 \times 10^{-8}$ | $12.7 \pm 0.310 \times 10^6$ |  |

Average myocyte volume in representative hearts from line 1 and line 58 was calculated utilizing measurements from myocyte cross-sectional areas and lengths. The number of myocytes per ventricle was calculated as the quotient of myocyte fraction of ventricular volume to the average myocyte volume.

As hyperplasia should be coupled with an increase in DNA synthesis, the inventors assayed the expression of proliferating cell nuclear antigen (PCNA) in normal and transgenic mice, at different stages, by immunohistochemical analysis. PCNA is a component of the DNA replication fork, and is required for both DNA synthesis and repair (Haracska et al., *Mol. Cell. Biol.*, 3:784-91,2002). The number of PCNA-stained nuclei per unit area was similar in both normal and transgenic mice, through E18; however, by PN2, there was a markedly higher level of expression in transgenic hearts than in normal hearts (FIG. 3D). This elevation in PCNA expression in transgenic hearts persisted to 6 months of age (a stage when PCNA expression is virtually undetected in non-transgenic hearts), albeit at more modest levels. These results suggested that cyclin A2 expression was correlated with an increase in DNA synthesis.

To examine the possibility that the increase in DNA synthesis could result in increased multinucleation of transgenic myocytes, cardiomyocyte nuclear density was measured by counting cardiomyocyte nuclei per unit area in transverse ventricular sections from adult (6 months) myocardium, taken from transgenic and non-transgenic littermates from lines 1 and 58. Cardiomyocytes were identified by staining with an antibody to α-sarcomeric actin, and DAPI was used to highlight nuclei. There was no significant change in the number of cardiomyocyte nuclei per unit area in transgenic hearts, as compared with normal hearts, for both lines 1 and 58. The numbers for line 1 were 32.70±1.86 in transgenic mice and 31.60±1.80 in normal mice. The corresponding numbers for line 58 were 30.60±1.76 in transgenic and 32.20±2.05 in normal mice. These data further support the conclusion that increased DNA synthesis in the transgenic hearts results in myocyte hyperplasia.

Because cyclin A2 regulates progression through the G2/M transition, in addition to the G1/S checkpoint of the cell cycle, the inventors sought to determine whether there was an increase in cardiomyocyte mitoses in the inventors' transgenic model. The expression of phosphorylated histone-3, a mitosis-specific marker, was assayed throughout development, in transgenic and normal hearts, utilizing an anti-phosphohistone-3 antibody. Phosphorylated histone-3 on Ser10 is an established marker for chromosome condensation during mitotic prophase in animal cells (Wei et al., *Proc. Natl. Acad. Sci.*, 95:7480-84, 1998). The phosphorylation of histone-3 begins in late G2, and is completed by early prophase; contrastingly, its dephosphorylation begins in anaphase, and is completed by early telophase (Hendzel et al., *Chromosoma*, 106:348-60, 1997).

Histologic sections from transgenic and non-transgenic hearts, at E18, PN2, PN7, PN14, and 6 months of age, were co-stained with antibody to α-sarcomeric actin, in order to localize the anti-phosphohistone-3-stained mitotic nuclei to cardiomyocytes. There was a significantly increased number of cardiomyocyte mitoses noted throughout all developmental time points examined (embryogenesis through post-natal stages) in the transgenic hearts (line 58) as compared with normal littermate hearts (FIG. 3E). The data from the 6-month time point are not shown, as there were only a few scattered mitoses noted in transgenic hearts, and none was noted in non-transgenic hearts. The most dramatic elevation in the number of mitoses in transgenic hearts, as compared with normal hearts, was noted at PN7, at which point there was an 8-fold increase in the number of mitotic divisions.

Figure 4:
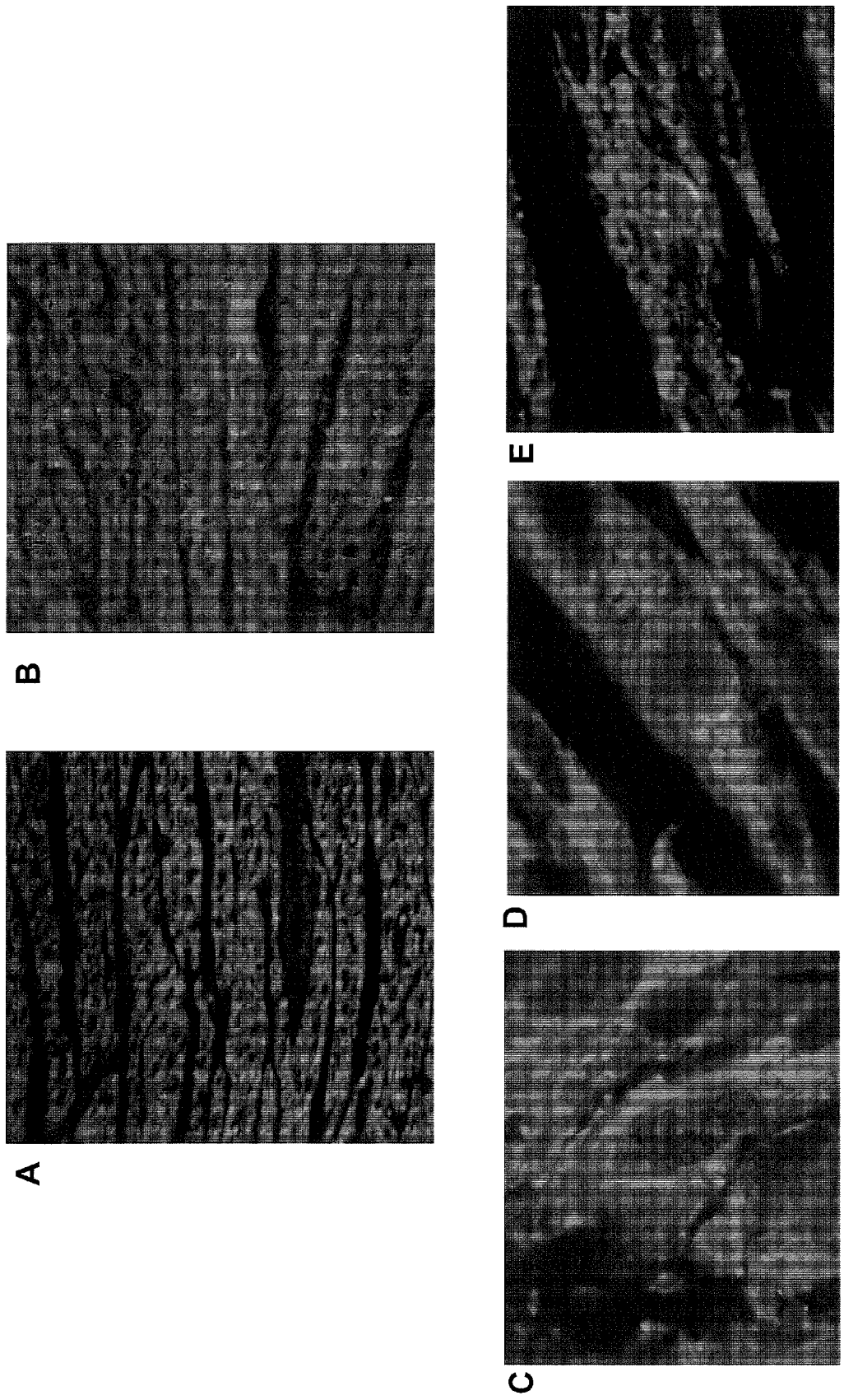
FIG. 4 depicts visualization of mitotic nuclei in ventricular myocardium from PN7 normal and transgenic mice. (A), (B) Immunofluorescence was used to localize H3P staining (red) and α-sarcomeric actin (green). Different stages of mitosis were observed in cardiomyocytes: (C) prophase, (D) prometaphase, and (E) likely anaphase.

Images obtained using confocal microscopy (similar ventricular sections of PN7, in non-transgenic (FIG. 4A) and transgenic (FIG. 4B) mice) illustrated the dramatic elevation in numbers of mitotic nuclei noted in the transgenic cardiomyocytes. Closer analysis with the confocal microscope revealed that several stages of mitosis—prophase, prometaphase, and (likely) anaphase—could be observed in transgenic cardiomyocytes, as illustrated in FIGS. 4C-4E. Rotational analysis of a 10-micron-thick histologic section further demonstrated the localization of a mitotic prometaphase nucleus, and ensured that it was embedded in an α-sarcomeric actin-stained cardiomyocyte (data not shown).

Figure 5:
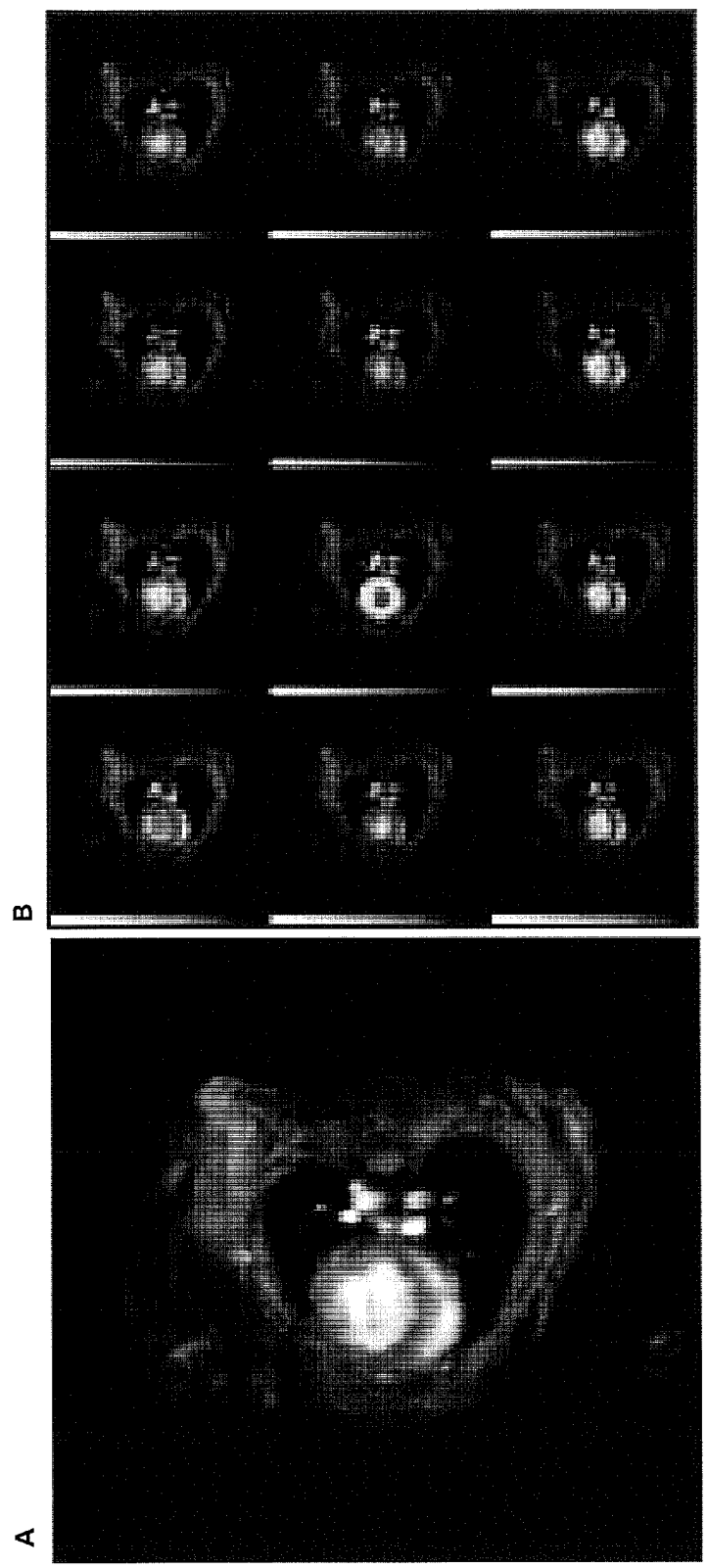
FIG. 5 illustrates an MRI analysis of cardiac function. (A) MRI image of a transgenic heart at a mid-ventricular cross-section of an 8-month old transgenic mouse. (B) MRI images of the heart at a mid-ventricular cross-section taken at different points in the cardiac cycle for the measurement of ejection fraction and fractional shortening. Ventricle in red indicates end-diastole, and ventricle in yellow indicates end-systole. (C) Ejection fraction and fractional shortening, as calculated from MRI analysis for normal (n=3) and transgenic (n=3) hearts.

Cardiac-function analysis was undertaken in transgenic (n=3) and non-transgenic littermate controls (n=3) from line 58 males, at 8 months of age, utilizing MRI (FIGS. 5A, 5B; data not shown). Ejection fraction was computed from the difference between the end-diastolic cavity area and the end-systolic cavity area, at mid-ventricular level. Fractional shortening was assessed by measuring thickening of the endocardium during systole (FIG. 5C). These indices are easily measured in murine MRI analysis, given the clear delineation between blood and the endocardial border. There was a mild, but statistically-significant, decrease in both ejection fraction and fractional shortening in the transgenic hearts, as compared with their littermate control hearts, at this time point. Echocardiographic analysis at an earlier time point (3 months of age) was performed among 3 lines for transgenic (n=6) and non-transgenic (n=6) mice, and there was no difference observed in fractional shortening (data not shown).

Example 9

Surgical Procedures

The following surgical procedures were used on mice that were studied in Examples 10-12. Cyclin A2 transgenic mice were maintained in a B6CBA background. Non-transgenic littermates and wild-type mice were used as two independent control groups. At 8 weeks of age, mice underwent LAD ligation to induce anterolateral MI. This was performed in a blinded manner. Each mouse was anesthetized and intubated, and subsequently underwent thoracotomy with LAD ligation under a surgical microscope. 30 transgenic mice, 31 non-transgenic mice, and 28 wild-type mice were infarcted with an overall 83% survival rate at 1 week post-infarct. There were no statistically-significant differences in mortality among the groups. All manipulations were performed according to Institutional Animal Care and Use Guidelines.

Example 10

Molecular Analysis

The infarcted mice from Example 9 were given weekly serial intraperitoneal bromodeoxyuridine (BRDU) injections, each at a concentration of 100 μg BRDU/g mouse. To examine response to the induced MI in the different groups, mice were sacrificed at 1 week, 2 weeks, 3 weeks, and 3 months of age, as follows. Each mouse was anesthetized with avertin. 3 M KCl was injected into the beating heart to induce diastolic arrest. The hearts were perfused with 1X phosphate buffered saline (PBS), and fat tissue was removed. The hearts were then fixed in 4% paraformaldehyde overnight. The atria were removed under a dissecting microscope. Thereafter, the ventricles were sectioned into serial 1-mm thick slices (with the first slice at the level of ligation of the LAD), dehydrated through ethanol series, and embedded in paraffin. Sequential transverse sections (5 μm) were then cut.

Co-immunofluorescence staining was performed utilizing anti-alpha-sarcomeric actin antibody with either anti-phosphorylatedhistone-3, anti-BRDU, anti-cyclin A2, or anti-ABCG2 antibody. Anti-mouse IgM FITC was used as the secondary antibody against alpha-sarcomeric actin for localizing nuclear proteins to cardiomyocyte nuclei. Rhodamine-conjugated antibody was used as the secondary against all other antibodies. Nuclei were stained with DAPI. Analysis was done under 40× and 100× magnification and fluorescent-field optics. 3-D analysis for definitive localization of signal to cardiomyocytes was performed using confocal microscopy.

The inventors detected cardiomyocyte mitoses in infarcted transgenic hearts only, and were able to localize these mitoses to cardiomyocytes utilizing antibody to alpha-sarcomeric actin. The inventors also observed an increase in DNA synthesis in infarcted transgenic hearts through BRDU labeling.

Figure 12:
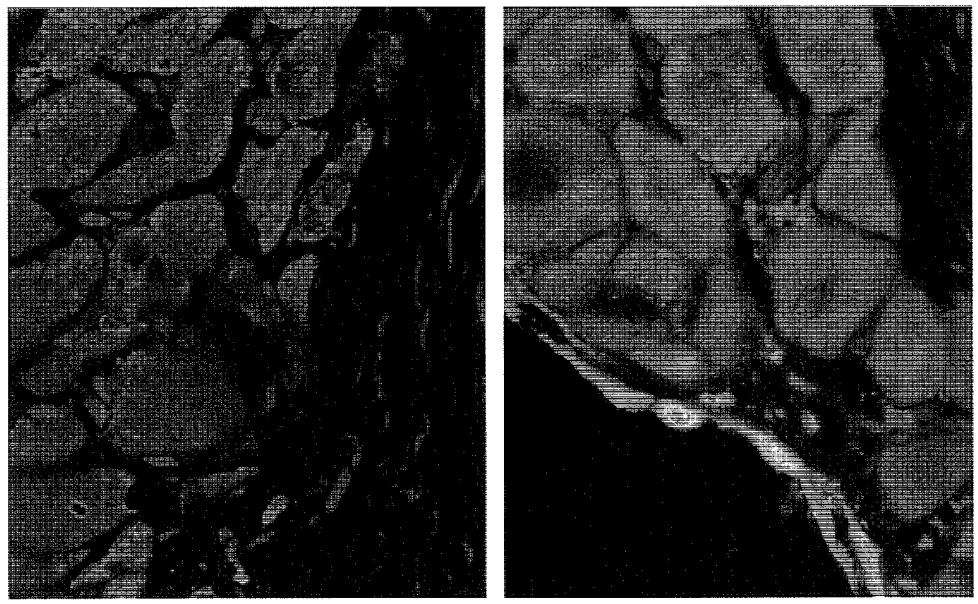
FIG. 12 depicts results of myocardial infarction. (A) Mitoses were not detected in wild-type infarcted hearts. Blue indicates DAPI; green indicates alpha-sarcomeric actin. (B) Abundant mitoses were detected in cardiomyocytes of transgenic infarcted hearts. Clusters of mitotic cardiomyocytes are shown in the transgenic infarcted myocardium. Red indicates phosphohistone-H3-positive nuclei. Phosphohistone-H3 (H3P) is a specific marker of mitosis. Blue indicates DAPI staining of nuclei. Green indicates the presence of alpha-sarcomeric actin, which is specific for cardiomyocyte cytoplasm. (C, D) Mitoses in the peri-infarct zone. (E, F) Small, immature cardiomyocytes in the infarct zone itself. The photographs show a high nuclear-to-cytoplasmic ratio: the nuclei appear mitotic, and the green fluorescence of the cytoplasm indicates the presence of alpha-sarcomeric actin. All photographs were taken on the confocal microscope; thus, the signals are very specific.
Figure 13:
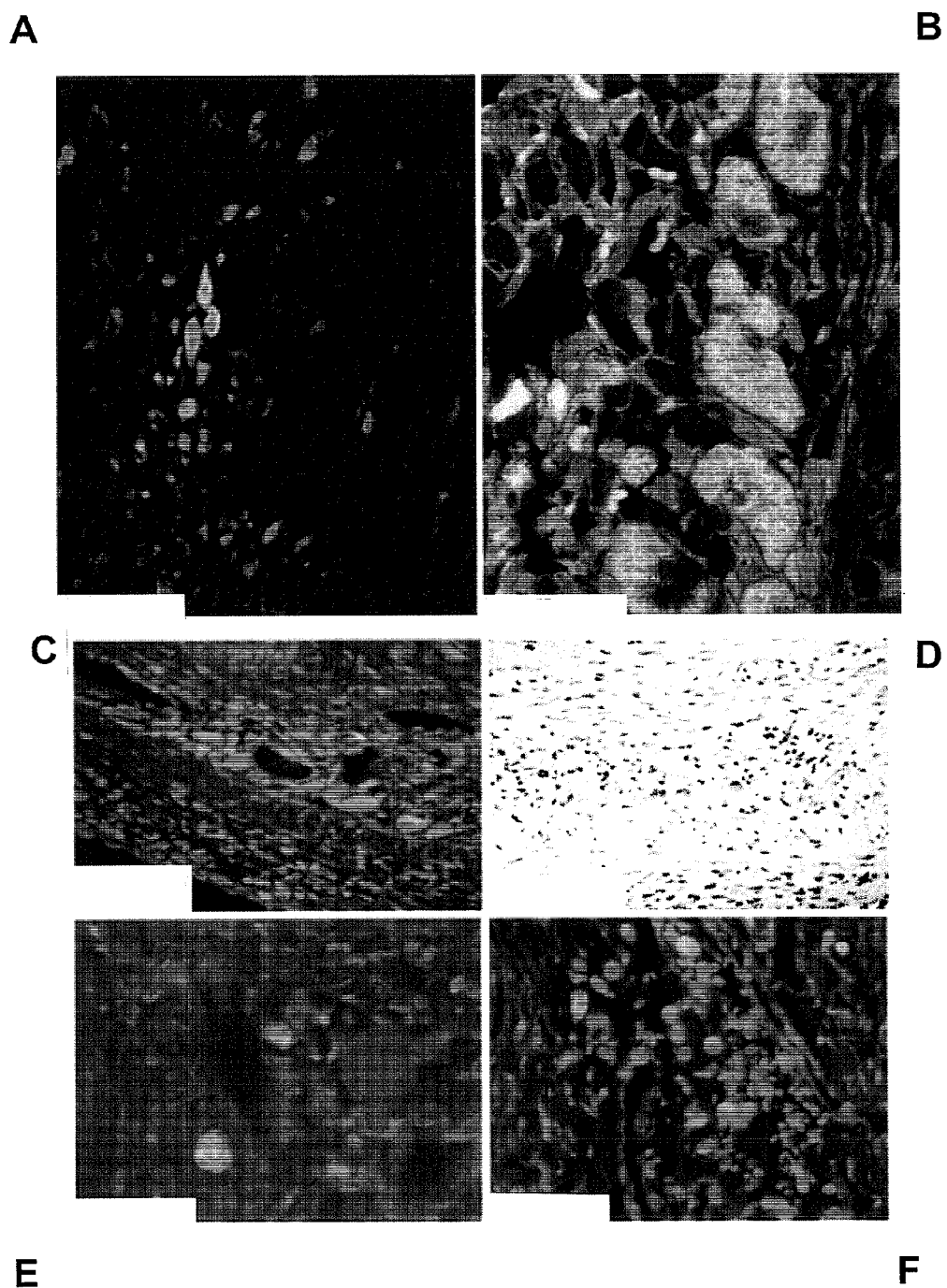
FIG. 13 illustrates detection of side-population (SP) progenitor cells in the mouse myocardium using ABCG2. ABCG2, a member of the ATP-cassette transporter family of proteins, is a marker of side-population progenitor cells found in mouse myocardium. Although the protein becomes ubiquitinated as cardiomyocytes proceed to differentiate, ABCG2 typically displays a membrane pattern of expression, and may be localized to the cytoplasm. The inventors utilized antibody to ABCG2, denoted by red in these photographs, to detect SP progenitor cells in infarcted mice. SP cells were noted in an equal number of transgenic and wild-type mice. However, ABCG2 was shown to have a membrane-staining pattern in some photographs, and a cytoplasmic location in other photographs. This suggests that the transgenic cells may be behaving differently from control cells. (A, E, F) ABCG2 shows a membrane-staining pattern. (B, C) ABCG2 has a cytoplasmic location. (D) ABCG2 is shown to have a cytoplasmic location. This light-microscopy photograph used DAB as a counterstain to ABCG2, in order to confirm that a non-specific, auto-fluorescent signal was not being detected.
Figure 14:
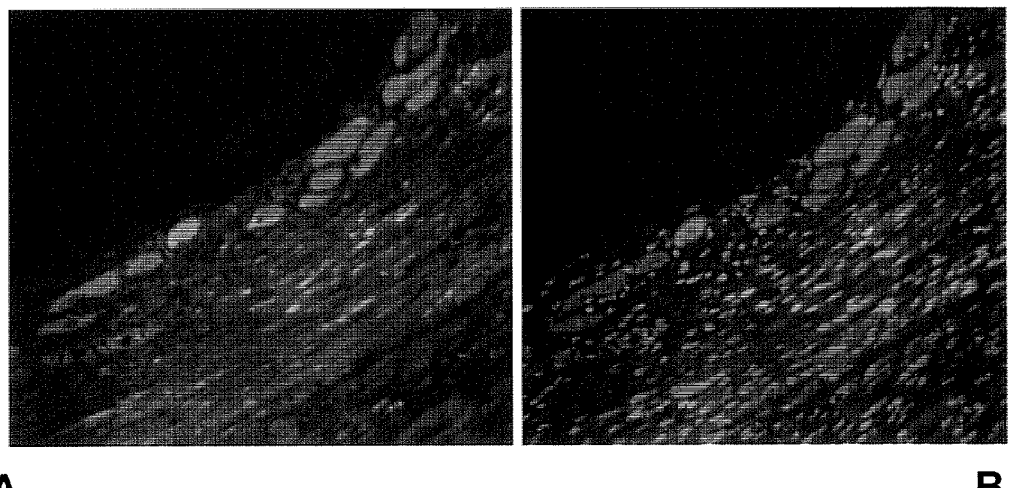
FIG. 14 illustrates nuclear localization of cyclin A2 in "de novo" myocardium of transgenic infarcted mice. Cyclin A2 was noted in the nuclei of what appear to be "de novo" myocytes in the infarct zone of the transgenic mice; this was not observed in controls. Furthermore, even in the transgenic mice, nuclear localization of cyclin A2 was not typically seen after early post-natal development (post-natal day 14); the transgene protein product was only noted in the cytoplasm at this point. (A) Red indicates cyclin A2; green indicates alpha-sarcomeric actin. (B) The section from (A) as viewed with a blue filter, so that the red signal of cyclin A2 can be localized to nuclei. The image from the blue filter was merged with the image from the green filter. Blue indicates DAPI staining of nuclei; green indicates alpha-sarcomeric actin.

Additionally, the inventors noted that ABCG2-positive (side-population progenitor) cells homed to the infarct region in several transgenic and control mice. These ABCG2-positive cells also appear to express alpha-sarcomeric actin, implying that they are differentiating into a cardiac lineage. Although these cells were noted in transgenics and controls, the nuclear localization of cyclin A2 was only observed in transgenic cardiomyocytes. In the normal heart, cyclin A2 is completely silenced at both the message and protein level after birth in rats, humans, and mice. In cyclin A2 transgenic mice, the cyclin A2 transgenic protein product is expressed in the nucleus only during the first two weeks after birth, and is localized to the cytoplasm thereafter. Results are shown in FIGS. 12-14.

Example 11

Assessment of Cardiac Function

MRI image acquisition was performed (in a blinded manner) on a 9.4 Tesla Bruker WB400 microimaging system, with 30-mm quadrature RF coil (Brucker NMR Inc., Bellerica, Mass.). The mice were anesthetized with isoflurane (1.5% volume in 2 L/min air flow). The heart rate was ~450 bpm. Quantification of ventricles was based on bright blood 2-D image stacks acquired using ECG-gated fast-gradient echo cine sequence. Functional magnetic resonance imaging (fMRI) was done at 1 week, 3 weeks, and 3 months post-MI. For calculation of volumetric ejection fraction, serial transverse sections were taken at 3 levels perpendicular to the vertical axis (from the apex to the aorta of the heart), and sagittal-section imaging was performed. The midline fMRI slice was also scanned using a tagging technique, in order to assess regional wall motion over time.

Based upon their MI studies, the inventors have determined that cyclin A2 transgenic mice have significantly better ejection fraction (EF) at both 3-week and 3-month timepoints, as compared with controls. The inventors have also observed that there is better regional wall motion in the transgenic mice; this may be quantified using the MRI tagging technique. Results are set forth in FIGS. 8-11.

Example 12

Assessment of Infarction Size

In order to determine the extent of infarction, 5-μm serial paraffin-embedded sections of the heart underwent Masson's trichrome staining. Imagetool (UTHSCSA, Texas) was utilized to measure the circumference of infarcted left ventricle (LV) relative to non-infarcted LV in each section. Based on these measurements and the mass of each slice used to generate the section, the infarction percent was calculated for each heart.

Figure 7:
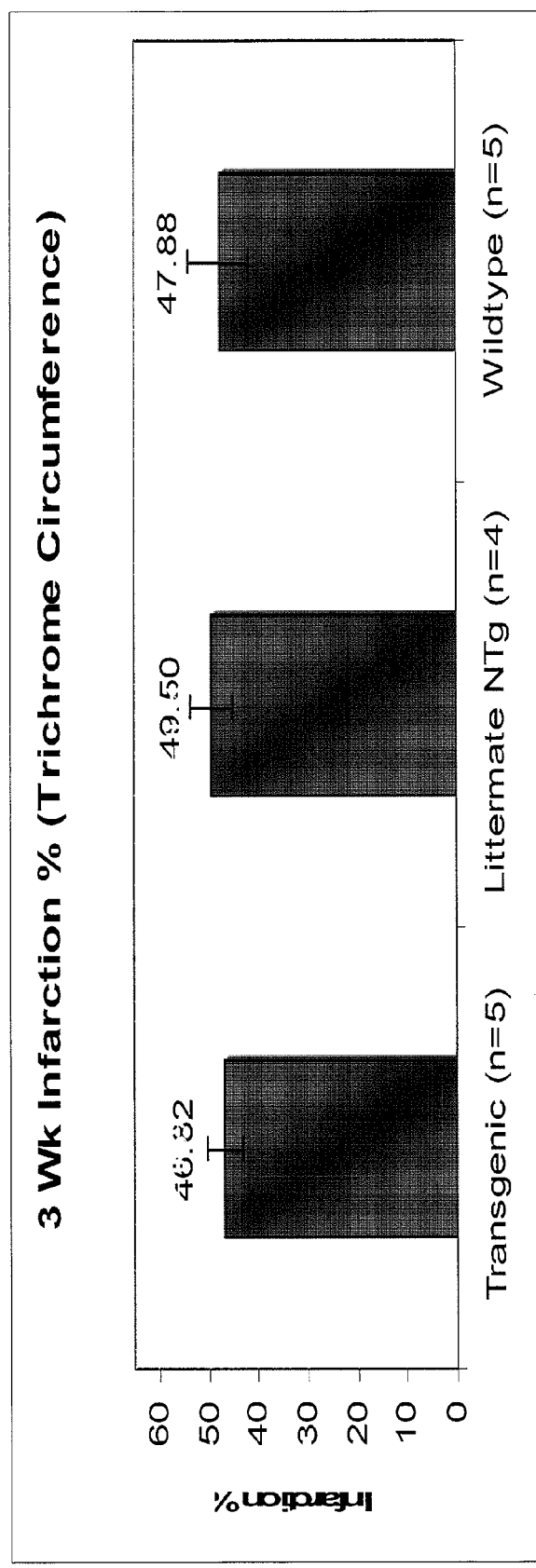
FIG. 7 shows the percent of left-ventricle-infarcted mice for all groups. This percentage was calculated by slicing each infarcted heart (from the ligation site to the apex) into 5 sections, measuring the mass of each slice, taking a thinner section from each slice (~5μm), and staining the slice with Masson trichrome to highlight areas of fibrosis. The ratio of the circumference of the infarcted area to the total circumference was multiplied by the mass of each slice, and the product of these was added for all 5 slices to obtain infarct volume percentage. The percentage of infarcted left ventricle was consistent between groups; thus, the inventors' surgical procedure was highly reproducible.
Figure 8:
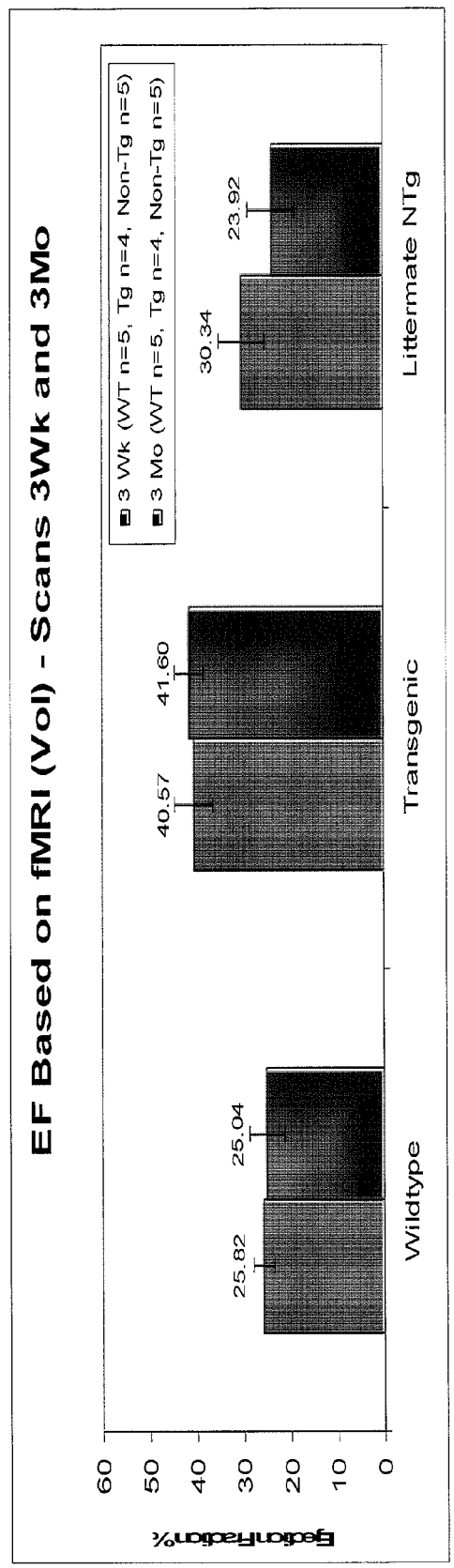
FIG. 8 illustrates the ejection fraction (EF) of infarcted mice for all groups that were assessed with serial MRI scans at 3 weeks and 3 months post myocardial infarction. The EF of the transgenic mice was significantly enhanced when compared to the EF of the wild-type controls and the non-transgenic littermate controls. EF was enhanced in transgenics, both at 3 weeks and 3 months post-infarct.
Figure 9:
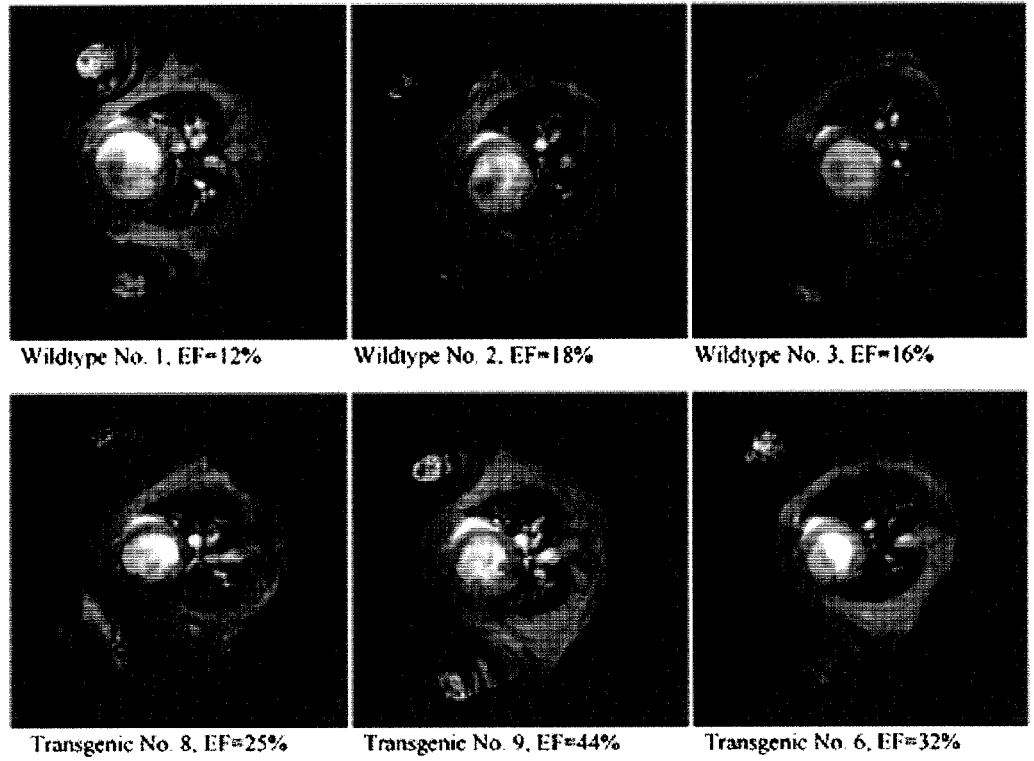
FIG. 9 sets forth representative MRI scans from 3 wild-type mice (top 3 panels) and 3 transgenic hearts (bottom 3 panels). The scans show less left ventricle (LV) cavity dilatation, and higher ejection fractions (EFs), in the transgenic hearts. Scans were taken at the mid-ventricular level, to demonstrate that the LV cavity size is notably smaller in the transgenic mice. The smaller cavity size is indicative of remodeling that is significantly less than that which was observed in wild-type animals. The EFs, computed volumetrically, are given for each respective mouse beneath each scan.
Figure 10:
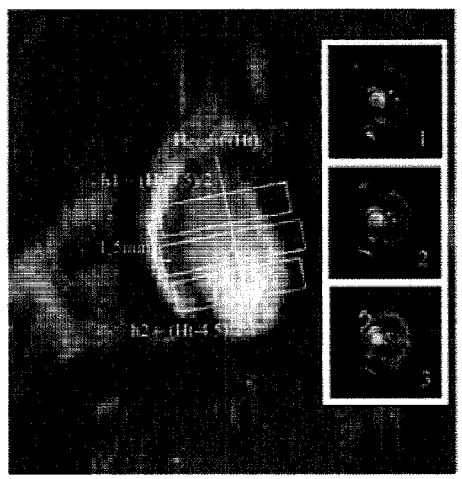
FIG. 10 illustrates volumetric EFs computed using 3 transverse images and 1 sagittal image. Three transverse images were scanned at equal distances from the mid-point of the long axis of the heart, as determined from a sagittal scan. It was assumed that the volume of an ellipsoid=4/3 Ah, where A=area and h=height; therefore, total volume=2/3 A1h1+ 1.5A1+1.5A2+1.5A3+2/3 A3h2. For each area (1, 2, 3), left-ventricular, end-systolic area was subtracted from left-ventricular, end-diastolic area, to obtain the volumetric EF.
Figure 11:
FIG. 11 demonstrates that MRI tagging may be utilized quantitatively to analyze changes in regional wall motion of infarcted groups. For a mid-ventricular scan, a grid of absent signal was applied while acquiring the scan. Strain deformation was then measured for a given point on the cross-hairs of this grid, between systole and diastole. Examination of serial images permits a determination as to whether regional wall motion (i.e., the infarcted wall) exhibits improvement in contractility over time.

Assessment of infarction size was repeated using gadolinium-enhanced multi-slice MR imaging. Gadolinium (0.1 ml 1:5 gado:saline 0.9%) was infused intraperitoneally, and images of hearts at the end of diastole were taken at 5 levels perpendicular to the vertical axis, for assessment of infarction size. The infarction region was determined based on the decreased regional wall motion shown in fMRI cine images; an estimation of infarction size, using the ratio between circumference of infarcted wall and circumference of non-infarcted wall, was made on the basis of 5 images. Results are shown in FIG. 7.

While the foregoing invention has been described in some detail for purposes of clarity and understanding, it will be appreciated by one skilled in the art, from a reading of the disclosure, that various changes in form and detail can be made without departing from the true scope of the invention in the appended claims.

---

What is claimed is:

1. A method of treating a subject, the method comprising administering to the subject a cyclin-associated agent in a manner sufficient to treat the subject,
wherein
the subject has heart tissue degeneration or is a candidate for heart tissue degeneration; and
the cyclin-associated agent is a nucleic acid encoding a Cyclin A2 protein in a manner permitting expression of the Cyclin A2 protein.

2. The method of claim 1, wherein the nucleic acid encodes a human cyclin A2.

3. The method of claim 1, wherein the nucleic acid is in a viral vector.

4. The method of claim 1, wherein the nucleic acid is operatively linked to a heart tissue-specific promoter.

5. The method of claim 1, wherein the nucleic acid is operatively linked to an inducible promoter.

6. The method of claim 1, wherein the subject is a human.

7. The method of claim 1, wherein the subject has heart failure.

8. The method of claim 1, wherein the subject has heart damage resulting from insufficient blood flow.

9. The method of claim 1, wherein the subject has chronic heart damage.

10. The method of claim 1, wherein the subject has damage resulting from a cardiotoxin.

11. The method of claim 1, wherein the subject has had a myocardial infarction.

12. The method of claim 1, wherein the subject is at risk for developing heart tissue degeneration.

13. The method of claim 1, wherein the cyclin-associated agent is administered to the subject by a catheter inserted into the subject's heart tissue.

14. The method of claim 1, wherein the cyclin-associated agent is administered to the subject by contacting the cyclin-associated agent with heart tissue cells or side-population progenitor cells of the subject in vivo.

15. The method of claim 1, wherein the cyclin-associated agent is administered to the subject by contacting the cyclin-associated agent with cells in vitro then introducing the cells into the subject.

16. The method of claim 15, wherein the cells are introduced into the subject through a catheter inserted into the subject's heart tissue.

17. The method of claim 15, wherein the cells are heart tissue cells or side-population progenitor cells.

18. The method of claim 15, wherein the cells are stem cells.

19. The method of claim 3, wherein the viral vector is a retrovirus, an HSV, an adenovirus, an adeno-associated virus, a Semiliki Forest virus, a cytomegalovirus, a lentivirus, or a vaccinia virus.

20. The method of claim 3, wherein the viral vector is an adenovirus, an adeno-associated virus, a lentiviruses or a retroviruses.

21. The method of claim 3, wherein the viral vector is an adenovirus or an adeno-associated virus.

22. A method of treating a subject that has heart tissue degeneration or is a candidate for heart issue degeneration, the method comprising administering a viral vector comprising a nucleic acid encoding a cyclin A2 protein to heart tissue cells of the subject in a manner sufficient to treat the subject.

\* \* \* \* \*

SEQUENCE LISTING

<160> NUMBER OF SEQ ID NOS: 1

<210> SEQ ID NO 1
<211> LENGTH: 422
<212> TYPE: PRT
<213> ORGANISM: Mus musculus

<400> SEQUENCE: 1

```
Met Pro Gly Thr Ser Arg His Ser Gly Arg Asp Ala Gly Ser Ala Leu
1               5                   10                  15

Leu Ser Leu His Gln Glu Asp Gln Glu Asn Val Asn Pro Glu Lys Leu
            20                  25                  30

Ala Pro Ala Gln Gln Pro Arg Ala Gln Ala Val Leu Lys Ala Gly Asn
        35                  40                  45

Val Arg Gly Pro Ala Pro Gln Gln Lys Leu Lys Thr Arg Arg Val Ala
    50                  55                  60

Pro Leu Lys Asp Leu Pro Ile Asn Asp Glu His Val Thr Ala Gly Pro
65                  70                  75                  80

Ser Trp Lys Ala Val Ser Lys Gln Pro Ala Phe Thr Ile His Val Asp
                85                  90                  95

Glu Ala Glu Glu Thr Gln Lys Arg Pro Ala Glu Leu Lys Glu Thr Glu
            100                 105                 110

Cys Glu Asp Ala Leu Ala Phe Asn Ala Ala Val Ser Leu Pro Ala Ala
        115                 120                 125

Arg Lys Pro Leu Thr Pro Leu Asp Tyr Pro Met Asp Gly Ser Phe Glu
```

-continued

```
               130                 135                 140
Ser Pro His Ala Met Asp Met Ser Ile Val Leu Glu Asp Lys Pro Val
145                 150                 155                 160

Asn Val Asn Glu Val Pro Asp Tyr Gln Glu Asp Ile His Thr Tyr Leu
                165                 170                 175

Arg Glu Met Glu Val Lys Cys Lys Pro Lys Val Gly Tyr Met Lys Arg
                180                 185                 190

Gln Pro Asp Ile Thr Asn Ser Met Arg Ala Ile Leu Val Asp Trp Leu
                195                 200                 205

Val Glu Val Gly Glu Glu Tyr Lys Leu Gln Asn Glu Thr Leu His Leu
                210                 215                 220

Ala Val Asn Tyr Ile Asp Arg Phe Leu Ser Ser Met Ser Val Leu Arg
225                 230                 235                 240

Gly Lys Leu Gln Leu Val Gly Thr Ala Ala Met Leu Leu Ala Ser Lys
                245                 250                 255

Phe Glu Glu Ile Tyr Pro Pro Glu Val Ala Glu Phe Val Tyr Ile Thr
                260                 265                 270

Asp Asp Thr Tyr Ser Lys Lys Gln Val Leu Arg Met Glu His Leu Val
                275                 280                 285

Leu Lys Val Leu Ala Phe Asp Leu Ala Ala Pro Thr Val Asn Gln Phe
                290                 295                 300

Leu Thr Gln Tyr Phe Leu His Leu Gln Pro Ala Asn Cys Lys Val Glu
305                 310                 315                 320

Ser Leu Ala Met Phe Leu Gly Glu Leu Ser Leu Ile Asp Ala Asp Pro
                325                 330                 335

Tyr Leu Lys Tyr Leu Pro Ser Leu Ile Ala Gly Ala Ala Phe His Leu
                340                 345                 350

Ala Leu Tyr Thr Val Thr Gly Gln Ser Trp Pro Glu Ser Leu Ala Gln
                355                 360                 365

Gln Thr Gly Tyr Thr Leu Glu Ser Leu Lys Pro Cys Leu Val Asp Leu
                370                 375                 380

His Gln Thr Tyr Leu Lys Ala Pro Gln His Ala Gln Gln Ser Ile Arg
385                 390                 395                 400

Glu Lys Tyr Lys His Ser Lys Tyr His Ser Val Ser Leu Leu Asn Pro
                405                 410                 415

Pro Glu Thr Leu Ser Val
                420
```